(12) United States Patent
Rich et al.

(10) Patent No.: US 11,147,531 B2
(45) Date of Patent: Oct. 19, 2021

(54) METHOD AND SYSTEM FOR MEASURING BLOOD PRESSURE USING ULTRASOUND BY EMITTING PUSH PULSE TO A BLOOD VESSEL

(71) Applicant: Sonetics Ultrasound, Inc., Ann Arbor, MI (US)

(72) Inventors: Collin A. Rich, Ypsilanti, MI (US); David Lemmerhirt, Ann Arbor, MI (US)

(73) Assignee: Sonetics Ultrasound, Inc., Ann Arbor, MI (US)

( * ) Notice: Subject to any disclaimer, the term of this patent is extended or adjusted under 35 U.S.C. 154(b) by 739 days.

(21) Appl. No.: 15/235,518

(22) Filed: Aug. 12, 2016

(65) Prior Publication Data

US 2017/0042504 A1 Feb. 16, 2017

Related U.S. Application Data

(60) Provisional application No. 62/204,064, filed on Aug. 12, 2015.

(51) Int. Cl.
*A61B 8/04* (2006.01)
*A61B 8/08* (2006.01)

(52) U.S. Cl.
CPC .............. *A61B 8/04* (2013.01); *A61B 8/0883* (2013.01); *A61B 8/0891* (2013.01)

(58) Field of Classification Search
CPC ......... A61B 8/04; A61B 8/089; A61B 8/0883; A61B 5/021; A61B 8/485
See application file for complete search history.

(56) References Cited

U.S. PATENT DOCUMENTS 4,030,485 A * 6/1977 Warner .................. A61B 5/021
600/480
4,109,642 A 8/1978 Reid et al.
(Continued)

FOREIGN PATENT DOCUMENTS

EP 666483 A 8/1995
EP 936144 A 8/1999
(Continued)

OTHER PUBLICATIONS

Ng et al., "Resolution in ultrasound imaging", 2011, Continuing Education in Anaesthesia, Critical Care & Pain, vol. 11, No. 5, pp. 186-192 (Year: 2011).*
(Continued)

*Primary Examiner* — Serkan Akar
(74) *Attorney, Agent, or Firm* — Jeffrey Schox

(57) ABSTRACT

A method and system for using ultrasound for evaluating pressure of a vessel of a user, the method including: providing an ultrasound system configured to be placed at a body region proximal the vessel of the user, generating a correlation between a set of push pulse parameters and a set of push pulse-dependent values associated with the vessel, wherein generating the correlation includes providing a push pulse and determining a push pulse-dependent value based on the push pulse, generating a pressure value from the vessel based on the correlation, and generating a pressure waveform from the pressure value and a set of supplemental pressure values.

21 Claims, 12 Drawing Sheets

(56) References Cited

U.S. PATENT DOCUMENTS

| | | | |
|---|---|---|---|
| 4,265,126 A | 5/1981 | Papadofrangakis et al. | |
| 4,327,739 A | 5/1982 | Chmiel et al. | |
| 4,906,837 A | 3/1990 | Doneen et al. | |
| 4,936,649 A | 6/1990 | Lymer et al. | |
| 5,440,936 A | 8/1995 | Spani et al. | |
| 5,462,059 A | 10/1995 | Ferrara et al. | |
| 5,535,747 A * | 7/1996 | Katakura | A61B 8/04 600/438 |
| 5,575,289 A | 11/1996 | Skidmore | |
| 5,873,830 A | 2/1999 | Hossack et al. | |
| 5,921,933 A | 7/1999 | Sarkis et al. | |
| 6,004,832 A | 12/1999 | Haller et al. | |
| 6,106,472 A | 8/2000 | Chiang et al. | |
| 6,142,946 A | 11/2000 | Hwang et al. | |
| 6,246,158 B1 | 6/2001 | Ladabaum | |
| 6,251,075 B1 | 6/2001 | Hashimoto | |
| 6,280,704 B1 | 8/2001 | Schutt et al. | |
| 6,292,435 B1 | 9/2001 | Savord et al. | |
| 6,314,057 B1 | 11/2001 | Solomon et al. | |
| 6,320,239 B1 | 11/2001 | Eccardt et al. | |
| 6,328,696 B1 | 12/2001 | Fraser | |
| 6,328,697 B1 | 12/2001 | Fraser | |
| 6,342,891 B1 | 1/2002 | Fenster et al. | |
| 6,361,499 B1 | 3/2002 | Bates et al. | |
| 6,375,617 B1 | 4/2002 | Fraser | |
| 6,428,469 B1 | 8/2002 | Iddan et al. | |
| 6,443,901 B1 | 9/2002 | Fraser | |
| 6,458,084 B2 | 10/2002 | Tsao et al. | |
| 6,461,299 B1 | 10/2002 | Hossack | |
| 6,506,156 B1 | 1/2003 | Jones et al. | |
| 6,506,160 B1 | 1/2003 | Van Stralen et al. | |
| 6,540,981 B2 | 4/2003 | Klaveness et al. | |
| 6,546,279 B1 | 4/2003 | Bova et al. | |
| 6,547,731 B1 | 4/2003 | Coleman et al. | |
| 6,562,650 B2 | 5/2003 | Ladabaum | |
| 6,605,043 B1 | 8/2003 | Dreschel et al. | |
| 6,610,012 B2 | 8/2003 | Mault | |
| 6,667,245 B2 | 12/2003 | Chow et al. | |
| 6,795,374 B2 | 9/2004 | Barnes et al. | |
| 6,939,531 B2 | 9/2005 | Schutt et al. | |
| 7,022,077 B2 | 4/2006 | Mourad et al. | |
| 7,030,536 B2 | 4/2006 | Smith et al. | |
| 7,314,445 B2 | 1/2008 | Wodnicki et al. | |
| 7,846,101 B2 | 12/2010 | Eberle et al. | |
| 8,162,837 B2 | 4/2012 | Moehring et al. | |
| 2002/0049375 A1 | 4/2002 | Strommer et al. | |
| 2002/0095087 A1* | 7/2002 | Mourad | A61B 5/0048 600/442 |
| 2003/0032211 A1 | 2/2003 | Ladabaum | |
| 2003/0055336 A1* | 3/2003 | Buck | A61B 8/06 600/453 |
| 2003/0114756 A1 | 6/2003 | Li | |
| 2003/0163046 A1 | 8/2003 | Nohara et al. | |
| 2003/0216621 A1 | 11/2003 | Alpert et al. | |
| 2004/0006273 A1 | 1/2004 | Kim et al. | |
| 2004/0133168 A1 | 7/2004 | Salcudean et al. | |
| 2004/0167403 A1* | 8/2004 | Nightingale | A61B 5/0053 600/437 |
| 2004/0179332 A1 | 9/2004 | Smith et al. | |
| 2004/0225220 A1 | 11/2004 | Rich | |
| 2005/0033177 A1 | 2/2005 | Rogers et al. | |
| 2005/0131294 A1 | 6/2005 | Ji et al. | |
| 2005/0143640 A1* | 6/2005 | Hoctor | A61B 8/04 600/407 |
| 2005/0154300 A1 | 7/2005 | Wodnicki et al. | |
| 2005/0177045 A1 | 8/2005 | Degertekin et al. | |
| 2005/0237858 A1 | 10/2005 | Thomenius et al. | |
| 2006/0036162 A1 | 2/2006 | Shahidi et al. | |
| 2006/0039105 A1 | 2/2006 | Smith et al. | |
| 2006/0058647 A1 | 3/2006 | Strommer et al. | |
| 2006/0058667 A1 | 3/2006 | Lemmerhirt et al. | |
| 2006/0079778 A1 | 4/2006 | Mo et al. | |
| 2006/0084966 A1 | 4/2006 | Maguire et al. | |
| 2006/0155174 A1 | 7/2006 | Glukhovsky et al. | |
| 2007/0038088 A1 | 2/2007 | Rich et al. | |
| 2007/0066897 A1 | 3/2007 | Sekins et al. | |
| 2007/0079658 A1 | 4/2007 | Wagner | |
| 2007/0167811 A1 | 7/2007 | Lemmerhirt et al. | |
| 2007/0167812 A1 | 7/2007 | Lemmerhirt et al. | |
| 2008/0071149 A1 | 3/2008 | Rich | |
| 2008/0071292 A1 | 3/2008 | Rich | |
| 2008/0249408 A1 | 10/2008 | Palmeri et al. | |
| 2008/0249419 A1 | 10/2008 | Sekins et al. | |
| 2008/0319316 A1 | 12/2008 | Powers et al. | |
| 2009/0149751 A1 | 6/2009 | Mourad et al. | |
| 2009/0250729 A1 | 10/2009 | Lemmerhirt et al. | |
| 2010/0087728 A1* | 4/2010 | Jarvik | A61B 5/0048 600/411 |
| 2010/0168577 A1* | 7/2010 | Vezina | A61B 5/02028 600/443 |
| 2010/0207485 A1 | 8/2010 | Dirksen et al. | |
| 2010/0217306 A1 | 8/2010 | Raabe et al. | |
| 2010/0241012 A1* | 9/2010 | Yin | A61B 5/055 600/485 |
| 2011/0151608 A1 | 6/2011 | Lemmerhirt et al. | |
| 2012/0010538 A1 | 1/2012 | Dirksen | |
| 2012/0116220 A1* | 5/2012 | Burcher | A61B 5/0048 600/438 |
| 2012/0283564 A1* | 11/2012 | Ebbini | A61B 8/06 600/439 |
| 2013/0096433 A1* | 4/2013 | Lemmerhirt | A61B 5/02007 600/441 |
| 2013/0158418 A1* | 6/2013 | Mizukami | A61B 8/0891 600/490 |
| 2013/0178736 A1* | 7/2013 | Pahlevan | A61B 5/022 600/492 |
| 2014/0187904 A1 | 7/2014 | Razani et al. | |
| 2015/0230718 A1* | 8/2015 | Whitaker | A61B 5/022 600/492 |
| 2016/0000398 A1* | 1/2016 | Raju | A61B 8/06 600/443 |
| 2016/0058409 A1* | 3/2016 | Mizukami | A61B 8/04 600/438 |
| 2016/0095572 A1* | 4/2016 | Aguren | A61B 8/04 600/438 |

FOREIGN PATENT DOCUMENTS

| | | |
|---|---|---|
| GB | 2272762 A | 5/1994 |
| JP | 2006526487 A | 11/2006 |
| JP | 2007222291 A | 9/2007 |
| JP | 2016027835 A | 2/2016 |
| WO | 2006123298 A | 11/2006 |
| WO | 2011064688 A1 | 6/2011 |
| WO | 2015029651 A1 | 3/2015 |

OTHER PUBLICATIONS

Doherty et al., "Acoustic Radiation Force Elasticity Imaging in Diagnostic Ultrasound," Apr. 2013, IEEE Transactions on Ultrasonics, Ferroelectrics, and Frequency Control, vol. 60, No. 4, pp. 685-701 (Year: 2013).*

Chen et al., "Design and Characterization of a CMOS Micromachined Capacitive Acoustic Sensor," Sensors 2007 IEEE Oct. 28-31, 2007.

Chen et al., "Design and Characterization of an Air-Coupled Capacitive Ultrasonic Sensor Fabricated in a CMOS Process," J. Micromech. Microeng. Jan. 18, 2008.

Cianci et al., "Improvements Towards a Reliable Fabrication Process for cMUT," Microelectr. Eng. 67-68, pp. 602-608 (2003).

Eccardt et al., "Micromachined Ultrasound Transducers with Improved Coupling Factors from a CMOS Compatible Process," Ultrasonics 38, pp. 774-780 (2000).

Glassman, "Concrete is Learning New Tricks, Like Letting in the Light," New York Times, Aug. 10, 2004.

Masoliver, "Concrete That Lets in Light," Insight Mar. 2000, p. 18 and 19.

Nadal-Guardia et al., "Constant Charge Operation of Capacitor Sensors Based on Switched-Current Circuits," IEEE Sensors J., vol. 3. No. 6 (Dec. 2003).

(56) References Cited

OTHER PUBLICATIONS

Westberg et al., "Surface Micromachining by Sacrificial Aluminum Etching," J. Micromech., Microneng. 6, pp. 376-387, printed in the UK (1996).
International Search Report and Written Opinion for application No. PCT/US2016/046729 dated Nov. 4, 2016.

* cited by examiner

METHOD AND SYSTEM FOR MEASURING BLOOD PRESSURE USING ULTRASOUND BY EMITTING PUSH PULSE TO A BLOOD VESSEL

CROSS-REFERENCE TO RELATED APPLICATIONS

This application claims the benefit of U.S. Provisional Application Ser. No. 62/204,064 filed 12 Aug. 2015, which is incorporated in its entirety herein by this reference.

TECHNICAL FIELD

This invention relates generally to the field of cardiovascular disease, and more specifically to a new and useful method and system for using ultrasound for assessment and management of cardiovascular disease.

DESCRIPTION OF THE PREFERRED EMBODIMENTS

Figure 1:
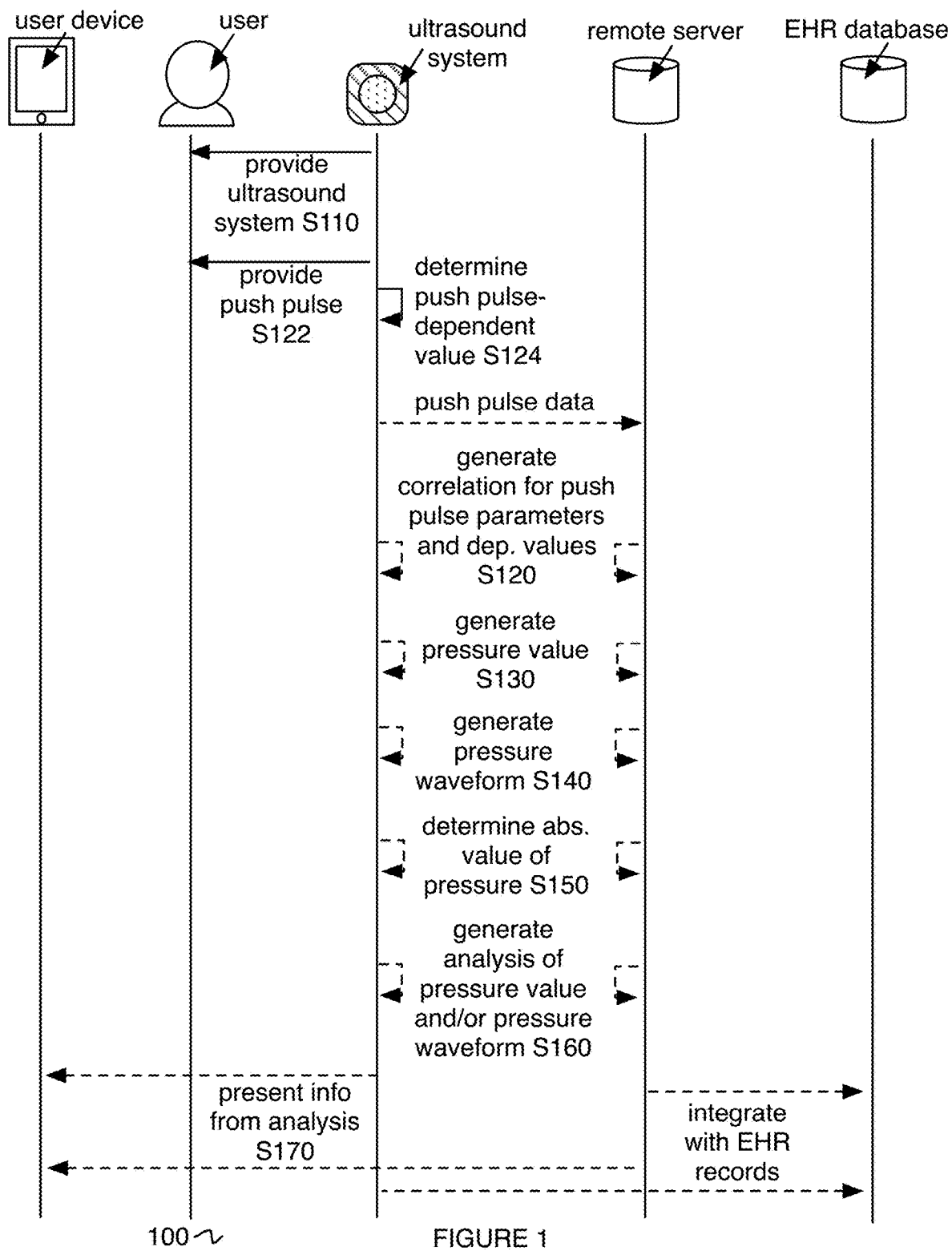
FIGS. 1-2, and 3A-3B depict application flows of embodiments of a method for using ultrasound in determining attribute values associated with a vessel of a user.
Figure 2:
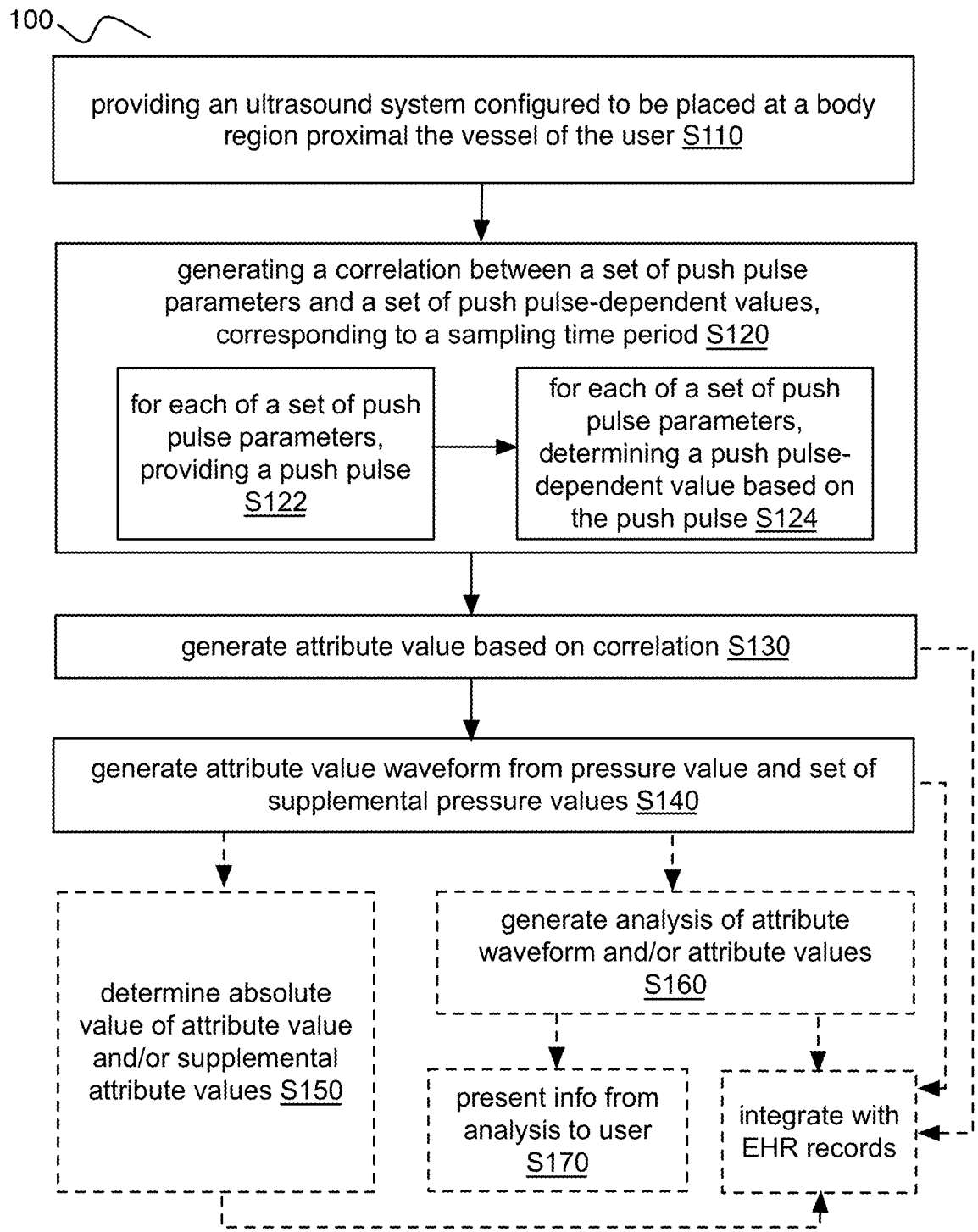

The following description of the preferred embodiments of the invention is not intended to limit the invention to these preferred embodiments, but rather to enable any person skilled in the art to make and use this invention.

1. Overview.

As shown in FIGS. 1-2 and 3A-3B, an embodiment of a method 100 for using ultrasound for evaluating pressure of a vessel of a user comprises: providing an ultrasound system configured to be placed at a body region proximal the vessel of the user S110; generating a correlation between a set of push pulse parameters and a set of push pulse-dependent values associated with the vessel S120; wherein generating the correlation includes providing a push pulse S122 (e.g., with the ultrasound system) and determining a push pulse-dependent value based on the push pulse S124; generating an attribute value associated with the vessel based on the correlation S130; and generating a pressure waveform from the pressure value and a set of supplemental pressure values S140. The method 100 can additionally or alternatively include determining an absolute value of a pressure value S150; generating an analysis of at least one of the pressure value and the pressure waveform S160; and presenting information derived from the analysis to the user at a user device S170. While variations of the method can be performed exclusively by an ultrasound system 210, other variations of the method can involve performance of portions of the method by any component of a system 200, including one or more of a remote server, a local processing system, a user device, a third party device, the ultrasound system 210 including a transducer 210, a processing system 220, a communications module 230, and/or a user interface 240, and/or any other suitable component.

In variations, the method 100 functions to leverage ultrasound technology to non-invasively evaluate cardiovascular disease-related health states of a user in a high-throughput and high-specificity manner. The method 100 can additionally or alternatively function to diagnose, monitor, recommend therapies, alert users and/or integrate with electronic health record (EHR) systems in relation to evaluated cardiovascular disease-related parameters (e.g., blood pressure, blood pressure variation over time, etc.). The method 100 is preferably performed with an embodiment, variation, or example of the system 200 in Section 4, but can alternatively be performed with any other suitable system.

2. Benefits.

In specific examples, the method 100 and/or system 200 can confer several benefits over conventional methodologies for determining cardiovascular parameters for managing cardiovascular disease. Traditional approaches involving a blood pressure cuff can be uncomfortable, difficult to administer, and limited to blood pressure at the arm of a user. Other traditional approaches such as cuffless pulse transit time (PTT) and pulse-wave velocity (PWV) for estimating cardiovascular parameters (e.g., blood pressure) can require complex, patient-specific calibration and compensation for changing vascular tone. However, in specific examples, the method 100 and/or system 200 can perform one or more of the following:

First, the technology can leverage ultrasound techniques to provide acoustic energy with a series of push pulses characterized by varying push pulse parameters (e.g., providing push pulses characterized by increasing push pulse pressures and/or pulse voltages) in order to provide a high-throughput approach for evaluating cardiovascular parameters of a user (e.g., a patient, a research subject, any suitable individual, etc.). For example, the technology can generate a plurality of measurements of cardiovascular health-relevant parameters within the span of a small number of heartbeats of a user. Additionally, the technology can generate highly specific cardiovascular parameters, with insensitivity to vascular tone and/or intervening tissue path of the patient. Further, the technology can be non-invasive, allowing for an improved user-experience for continuous monitoring in generation of cardiovascular parameter waveforms (e.g., a continuous time-varying blood pressure waveform), where the technology can be operated by a user without training and/or device calibration.

Second, the technology can determine cardiovascular health-relevant parameters associated with any suitable body region of the user. The technology can be configured to couple one or more regions of the user's arm, head, torso, neck, and/or any other user body region, thereby facilitating evaluation of cardiovascular health-relevant parameters associated with the body region(s). Vascular diseases such as thrombosis, aneurysms, and atherosclerosis can be better monitored through generation and analysis of cardiovascular parameters associated with body regions in addition to or other than a patient's arm (e.g., as in a traditional cuff-based system).

Third, the technology can provide a full-stack approach including diagnosis, continuous monitoring, therapy recommendation, and response management in relation to cardiovascular health. For example, the technology can be used by a user in any suitable setting (e.g., at home, at work, during physical activity, etc.), to monitor cardiovascular health. Generated cardiovascular parameters and/or supplemental data (e.g., patient demographic information, patient behavioral information, electronic health records, etc.) can be analyzed in providing risk and/or severity values associated with different cardiovascular diseases (e.g., hypertensive heart disease, rheumatic heart disease, ischemic heart disease, cerebrovascular disease, inflammatory heart disease, etc.) to a user and/or third party (e.g., a healthcare provider, a guardian, family, friends, etc.). Based on the generated cardiovascular parameters, supplemental information, and/or diagnostic analysis, therapy recommendations can be generated (e.g., recommended medication, treatment procedures, lifestyle changes, etc.) and/or automatically implemented (e.g., through an automatic medication dispenser, fulfillment of prescriptions, scheduling of care provider appointments, alerts and/or reminders on a mobile device of the user, etc.). Additionally or alternatively, treatment responses can be measured and/or monitored, for example, utilizing the same ultrasound technology and push pulse methodologies.

Fourth, the technology can be used in evaluating parameters (e.g., pressure parameters) of any suitable vessel, including both biological and non-biological vessels. For example, the technology can be used in measuring a pressure of an underground storage tank with a compliant pressure-transmissive medium. The technology can accommodate a variety of mediums through varying ultrasound transducer and/or push pulse parameters. In another example, the technology can be used with frequencies in the subsonic range (e.g., as used in SONAR) for geological purposes in measuring pressure of underground aquifiers and/or oil deposits.

The technology can, however, provide any other suitable benefit(s) in the context of using ultrasound hardware for evaluating properties of biological and/or non-biological vessels.

3. Method.

As shown in FIGS. 1-2 and 3A-3B, an embodiment of a method 100 for using ultrasound for evaluating pressure of a vessel of a user comprises: providing an ultrasound system configured to be placed at a body region proximal the vessel of the user S110; generating a correlation between a set of push pulse parameters and a set of push pulse-dependent values associated with the vessel S120; wherein generating the correlation includes providing a push pulse S122 and determining a push pulse-dependent value based on the push pulse S124; generating an attribute value associated with the vessel based on the correlation S130; and generating a pressure waveform from the pressure value and a set of supplemental pressure values S140.

In some variations, the method 100 can additionally or alternatively include determining an absolute value of a pressure value S150; generating an analysis of at least one of the pressure value and the pressure waveform S160; and presenting information derived from the analysis to the user at a user device S170.

3.1 Providing an Ultrasound System.

Block S110 recites: providing an ultrasound system configured to be placed at a body region proximal the vessel of the user, which functions to provide a system with for perturbing and measuring perturbations in relation to a vessel of the user, for evaluating cardiovascular parameters. A transducer of the ultrasound system is preferably coupled to the body region of the user, but any suitable component of the ultrasound system and/or other system can be additionally or alternatively coupled to the body region of the user. A component of the ultrasound system is preferably placed at the exterior portion (e.g., outside skin) of the body region, but portions of components of the ultrasound system can be placed and/or embedded within a body region (e.g., subcutaneously, etc.). Providing an ultrasound system can include coupling the ultrasound system to a user through a coupling agent. Coupling agents can include any combination of a coupling gel, water, mineral oil, petrolatum, and/or any other suitable agent. However, a coupling agent can be omitted in providing an ultrasound system to be placed at a user's body region. The ultrasound system coupled with the user preferably possesses a substantially constant coupling efficiency between the ultrasound transducer and the outer surface of the interstitial media. Additionally or alternatively, the coupling efficiency can vary (e.g., during vigorous physical activity, when the user is in a water-based environment such as when the user is taking a shower, etc.). In variations, variances in coupling efficiency can be accounted for by the ultrasound system (e.g., by detecting an uncoupling state between an ultrasound transducer and the user, alerting the user of the uncoupling state and/or automatically providing an actuating force to recouple the ultrasound transducer to the user; by processing the measurements to account for coupling inefficiencies, etc.). However, coupling between the ultrasound system and the user can possess any suitable coupling efficiency with any suitable variance (e.g., over time and/or other suitable variables).

With respect to Block S110, components of the ultrasound system are preferably placed at body regions of the user that are proximal a vessel of the user. Vessels can include a blood vessel (e.g., artery, capillary, vein, etc.), a heart chamber, bladder, and/or any other suitable physiological region associated with cells, tissues, organs, and/or organ systems of the user. As shown in FIGS. 11, 12A-12C, and 13A-13D, vessels can include a pressure-transmissive medium (e.g., blood, urine, etc.) for measurement and analysis as in Blocks S120, S130, and S140. In particular, vessels are preferably surrounded by interstitial media including a path at least partially transmissive of ultrasound (e.g., acoustic pressure in the range of 400 kHz-80 MHz), the path preferably extending from the user surface (e.g., skin surface) coupled with the ultrasound transducer to approximately the depth of a vessel wall. However, a vessel can be located at any location with respect to a user's body, and/or can possess any suitable relationship to other physiological matter of the user. Components of the ultrasound system can be placed at body regions including the user's arm (e.g., near internal vessels of the hand, near a radial artery, near a brachial artery, etc.), head (e.g., outside an eyelid, near a temple, etc.), torso (e.g., at a suprasternal notch, near an aortic arch, etc.), neck (e.g., near a carotid artery, etc.), and/or any other internal and/or external body region of the user.

Regarding Block S110, providing an ultrasound system is preferably performed in a non-invasive manner without requiring introduction of device components into the user. Non-invasively providing the ultrasound system to the user can include providing a non-invasive ultrasound system configured to be placed on an exterior body region of the user without penetration of the skin of the user. However, non-invasively providing the ultrasound system can be performed in any suitable fashion. The ultrasound system can be provided to a user at home, work, at a social activity, in a research setting, in a healthcare setting (e.g., at a hospital), and/or at any suitable location. In examples, an ultrasound system can be provided to a user upon recommendation and/or approval by a care provider (e.g., by a physician recommending the ultrasound system for blood pressuring monitoring), in response to a purchase order by a user, and/or through any other suitable medium. However, different components of the ultrasound system can be provided to the user in different contexts and/or at different time points (e.g., providing ultrasound components required to measure and record data at a first time period for continuous long-term monitoring, and subsequently providing a communications module of the ultrasound system at a second time period for transmission of the recorded data), and/or components of the ultrasound system can be otherwise provided in relation to time and user situation.

In a variation of Block S110, providing an ultrasound system can include self-calibrating the ultrasound system based on the body region at which the ultrasound is placed. Self-calibrating the ultrasound system preferably facilitates determination of internal vessel pressures of a user without requiring the user to perform supplemental calibration operations with the device. Alternatively, calibration of the ultrasound system can include detecting an uncalibrated status of the ultrasound system, presenting the user with a set of instructions at the user interface, the set of instructions configured to prompt the user to perform a series of operations for calibrations of the ultrasound system. In this variation, calibration of the ultrasound system can be based on point of contact (e.g., an interfacing region between the ultrasound system and the body region of the user) between the ultrasound system (e.g., a transducer of the ultrasound system) and the user, on time of use, environmental conditions (e.g. humidity, temperature, moisture, etc.), and/or any other suitable condition. However, calibrating the ultrasound system can be performed in any suitable manner. For example, Block S110 can include calibrating the ultrasound system with an external and/or internal pressure reference standard.

In another variation of Block S110, an ultrasound system can be placed proximal a non-biological vessel. The non-biological vessel can have an association or no association with a body region of a user. For example, non-biological vessels associated with a body region of a user can include medical devices (e.g., implanted medical devices, external medical devices, etc.), prostheses, wearable devices, and/or any other suitable non-biological vessel. Non-biological vessels with no association to a body region of a user can include underground components (e.g., storage tanks, aquifiers, oil deposits, etc.), underwater components, and/or any other suitable non-biological vessel. However, any components of the ultrasound system can be placed proximal any suitable non-biological vessel for measurement of properties of the non-biological vessel.

Additionally or alternatively, providing an ultrasound system can include embodiments, variations, examples and/or any elements described in U.S. application Ser. No. 13/655,191 entitled "System and Method for Unattended Monitoring of Blood Flow," filed 18 Oct. 2012, and U.S. application Ser. No. 13/854,824, entitled "Ultrasound System and Method of Manufacture", filed 1 Apr. 2013, which are herein each incorporated in their entirety by this reference. However, providing an ultrasound system can be performed in any other suitable fashion.

3.2 Generating a Correlation.

Block S120 recites: generating a correlation between a set of push pulse parameters and a set of push pulse-dependent values, which functions to correlate push pulse parameters with values measured in response to providing push pulses characterized by the push pulse parameters, in order to extract one or more attribute values (e.g., an internal pressure) associated with a corresponding vessel of the user. Block S120 can additionally or alternatively include providing a push pulse S122 (or multiple push pulses) and determining a push pulse-dependent value (or multiple push pulse values) based on the push pulse(s) S124.

With respect to Block S120, push pulse parameters can include any combination of: push pulse pressure, push pulse voltage, orientation (e.g., of an ultrasound system component, of acoustic energy transmitted by the ultrasound system, of a push pulse, etc.) to vessel, push center frequency, push pulse focus, push pulse depth, push pulse intensity, push pulse packet length, waveform sampling rate, number of packets per push step, inter-step rest (e.g., time between push pulse voltage steps when providing a series of push pulses), imaging center frequency, push pulse shape, acoustic energy shape (e.g., planar, focused, etc.), location of measuring a push pulse-dependent value (e.g., location for evaluating displacement of the vessel in response to provision of a push pulse), displacement characteristic (e.g., axial distance, lengthwise radius of displaced vessel region, crosswise radius of displaced region, etc.), displacement measurement technique (e.g., speckle tracking, tissue Doppler, etc.), probe orientation (e.g., in relation to vessel), and/or any other suitable push pulse parameter.

Figure 5:
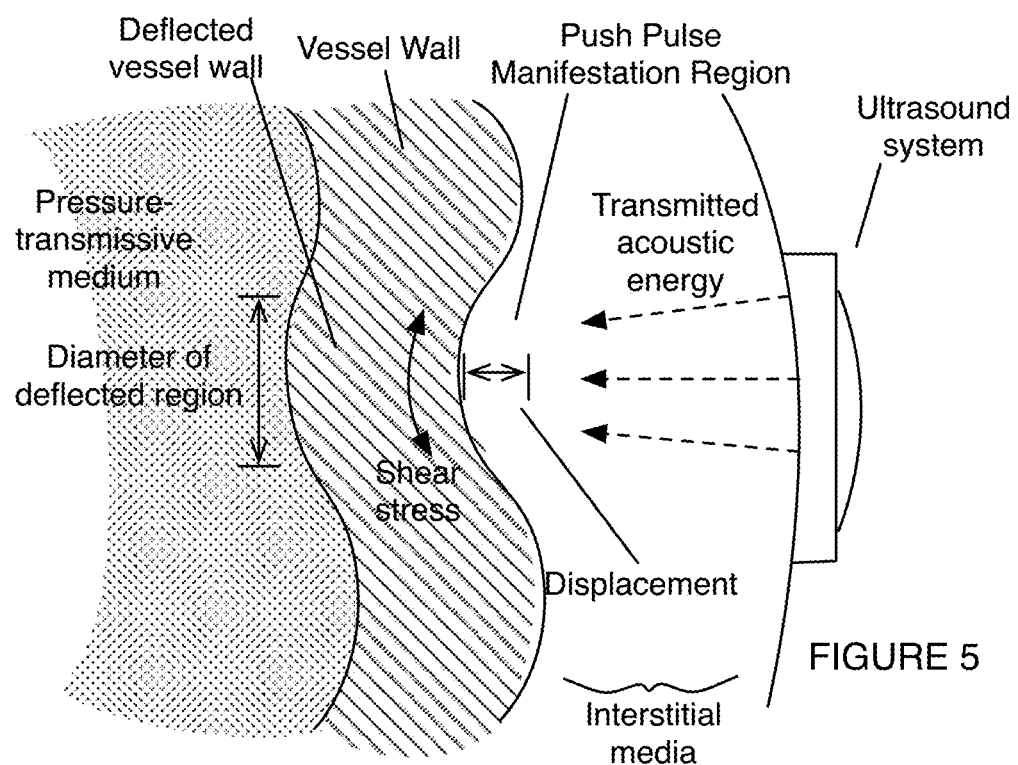

In Block S120, push pulse-dependent values can include any combination of: vessel morphological aspects (e.g., displacement of a vessel in relation to a push pulse perturbation compared to no perturbation, diameter of the vessel, length of the vessel, vessel wall morphological characteristics such as thickness, etc.), mechanical properties (e.g., stress, strain, stress-strain relationships, strength, stiffness, viscoelastic properties, shear elasticity modulus, Young's modulus, dynamic shear viscosity, anisotropy, non-linearity, etc.), vessel fluid aspects (e.g., fluid flow behavior, flow velocity, density, weight, viscosity, chemical properties, pH, composition, etc.), physical properties (e.g., temperature properties, phase, density, solubility, vapor pressure, electrical conductivity, etc.), and/or any other suitable push pulse-dependent values associated with a vessel. Displacement of the vessel can include displacement exclusively caused by one or more push pulses, overall displacement during a time period (e.g., during a sampling time period including provision of one or more push pulses), displacement along any suitable axis and/or plane, and/or can be defined in any suitable manner. As shown in FIG. 5, displacement of the vessel can be defined as displacement along an axis approximately parallel to an transmitted acoustic energy path. In other examples, displacement of the vessel can include displacement along an axis perpendicular a transmitted acoustic energy path, displacement along a plane intersecting an ultrasound system providing the push pulse, displacement along an axis approximately perpendicular a longitudinal axis of the vessel, and/or any suitable measure of displacement in relation to the vessel, the ultrasound system, surrounding locations, and/or any other suitable component. Correlations between push pulse parameters and push pulse dependent values can include positive correlations, negative correlations, weak correlations, perfect correlations, no correlation, and/or any other suitable correlation with any correlation coefficient value.

Figure 7A:
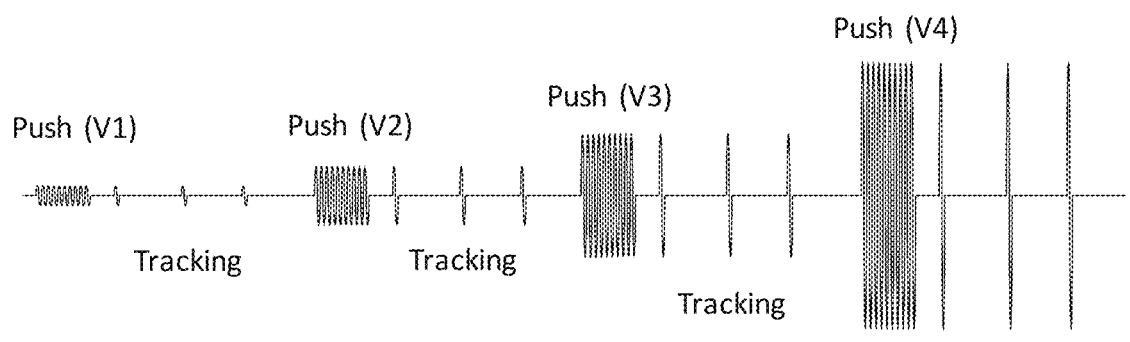
FIGS. 7A-7C depict graphical representations of a push pulse sequence characterized by ramping push voltage.
Figure 7B:
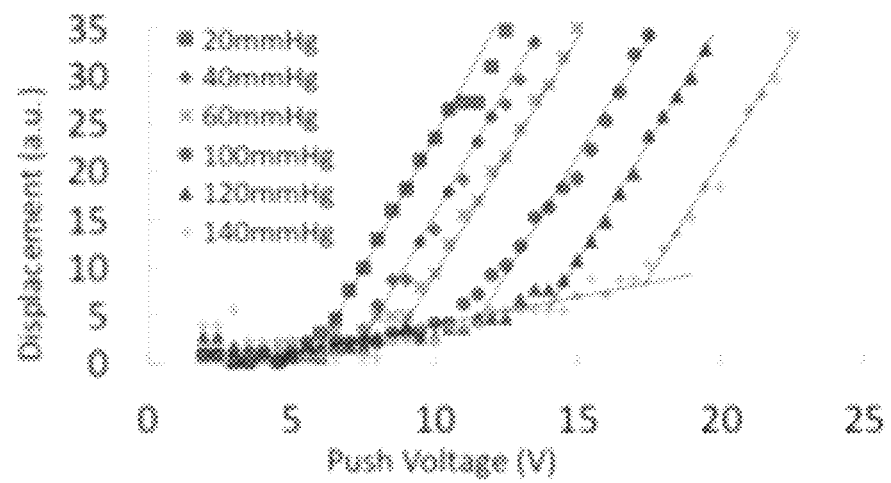
Figure 7C:
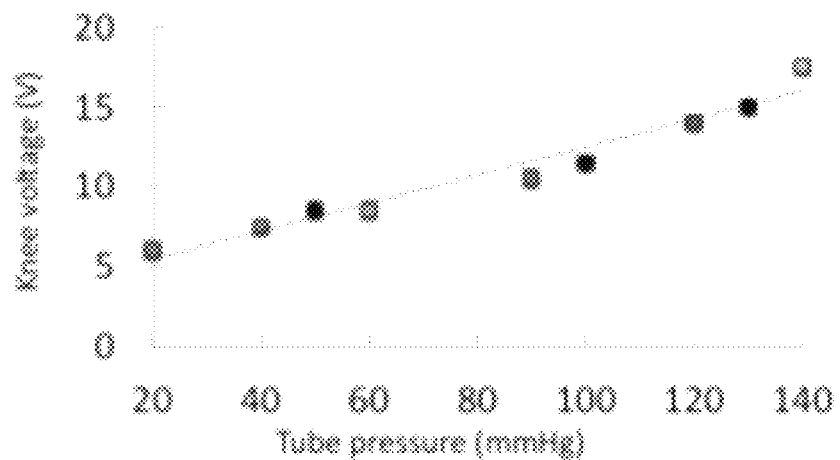

In Block S120, generating a correlation can include fitting a curve (e.g., a line, a polynomial function, Gaussian functions, Lorentzian functions, Voigt functions, any suitable function, etc.) to the set of push pulse parameters and the set of push pulse-dependent values. Additionally or alternatively, Block S120 can include fitting push pulse parameters and/or push pulse-dependent values to an a priori known, piecewise curve template. Correlations are preferably generated between push pulse parameters and push pulse-dependent parameters, but can be generated between any suitable data of Blocks S122, S124, S130, S140, S150, and/or any suitable data in relation to the method 100. In an example, Block S120 can include generating a curve template (e.g., used for determining a transition region) by: collecting a plurality of sets of push pulse parameters (e.g., characterizing emitted push pulses by an ultrasound system) and corresponding push pulse-dependent values (e.g., displacement values measured from blood vessel displacement); for each of the plurality of sets of push pulse parameters and corresponding push pulse-dependent values, generating a correlation between the set of push pulse parameters and corresponding push pulse-dependent values; and averaging the correlated sets from the plurality of sets of push pulse parameters and corresponding push pulse-dependent values. Generating a correlation between push pulse parameters and push pulse-dependent parameters can be performed by allowing shifts only on the push-parameter axis, and scaling on the push pulse-dependent values axis, but can otherwise be performed in any suitable manner. However, any suitable correlation and/or correlation-related operation can be performed. In a variation, push pulse parameters can be associated with displacement of the vessel in response to provision of a push pulse locally manifesting proximal the vessel. In a specific example of the variation, Block S120 can include generating a correlation between a set of push pulse pressure parameters and a set of displacement values associated with the blood vessel. In another specific example of the variation, Block S120 can include can include generating a correlation between a set of push voltage parameters and a set of displacement values associated with the blood vessel. As shown in FIGS. 7A-7C, in this specific example, the correlation can be generated from values measured in response to a push pulse sequence characterized by ramping push voltages. However, push pulse parameters, push pulse-dependent values, and/or correlations can be configured in any suitable fashion.

As to Block S120, generated correlations can be used for extrapolation (e.g., linear extrapolation, non-linear extrapolation, polynomial extrapolation, conic extrapolation, French curve extrapolation, etc.) and/or interpolation (e.g., linear interpolation, non-linear interpolation, polynomial interpolation, spline interpolation, piecewise constant interpolation, and/or any suitable form of interpolation) of push pulse-dependent values (e.g., using a known push pulse parameter and a correlation between push pulse parameters and push pulse-dependent values), push pulse parameters (e.g., using a measured push pulse-dependent value and a correlation between push pulse parameters and push pulse-dependent values), vessel attribute values, and/or any other suitable values in relation to the method 100. In examples where a correlation is generated between internal vessel pressures (e.g., determined as in Block S130) and vessel displacement in response to provided push pulses, internal vessel pressures (e.g., blood pressure) can be extrapolated and/or interpolated using a known vessel displacement and the correlation. However, generated correlations can be used in any suitable manner.

Regarding Block S120, generated correlations preferably correspond to a sampling time period, but can additionally or alternatively correspond to, be associated with, and/or have any suitable relationship with any suitable temporal indicator (e.g., a time point, time window, time period, duration, etc.). A sampling time period preferably includes temporal indicators (e.g., time windows, time points, etc.) corresponding to provision of the push pulses characterized by the set of push pulse-dependent values. For example, for a set of push pulse parameters including push voltages of 5, 10, 15 and 20, the sampling time period would include time windows corresponding to when the push pulses were provided according to the push voltages (i.e., at 5V, 10V, 15V, and 20V). Additionally or alternatively, push pulse parameters, push pulse-dependent values, and/or any suitable data of the method 100 can be associated with any suitable temporal indicator.

In relation to Block S120, all of or portions of generating a correlation are preferably performed after and/or in response to placement of the ultrasound system at the body region of the user. Blocks S120, S122, and/or S124 can be manually initiated (e.g., by a patient, by a care provider, by a researcher, by any suitable user etc.). Additionally or alternatively, Blocks S120, S122, and/or S124 can be automatically catalyzed based on predetermined rules (e.g., providing push pulses, measuring responses, and generating correlations at specified time intervals, etc.), user preferences (e.g., a user selects an option for continuous monitoring only during the daytime, etc.), and/or through any suitable criteria. In a variation, automatically performing Block S120, S122, and/or S124 can be in response to assessing conditions using a machine learning model (e.g., implemented with a machine learning algorithm described in Section 4), and/or models including probabilistic properties, heuristic properties, deterministic properties, and/or any other suitable properties for determining suitable conditions for providing a push pulse S122, measuring a push pulse-dependent parameter S124, and/or generating a correlation S120. Such models can leverage inputs including environmental conditions (e.g., temperature, humidity, time of day, light characteristics, audio characteristics, etc.), preliminary measurements (e.g., of cardiovascular parameters, etc.), data characteristics (e.g., sufficiency of collected data, types of collected data, amount of collected data, data required for generating values for target cardiovascular parameter types, etc.), ultrasound system status (e.g., battery life, body region placement, coupling efficiency, etc.), and/or any other suitable inputs for generating outputs relating to determination of whether and/or when to perform Blocks S120, S122, and/or S124. However, such portions of the method can be performed at any suitable time.

For Block S120, generating a correlation can be performed at one or more of: the ultrasound system (e.g., a processing subsystem of the ultrasound system), a user device (e.g., mobile computing device, wearable computing device), a care provider device, a remote server, and any other suitable processing component. Any of the aforementioned components can additionally or alternatively be utilized for storing generated correlations. As such, in variations, generating a correlation S120 can include: in response to generating the correlation, transmitting the correlation to a remote server for storage and processing as in Blocks S130, S140, S150, and/or S160. Generated correlations and/or any of the correlation constituents (e.g., correlated push pulse parameters, correlated push pulse-dependent parameters, etc.) can be associated with a user (e.g., user account, user profile), a population (e.g., a patient subgroup sharing similar demographic characteristics, behavioral characteristics, symptoms, vessel attribute values, etc.), EHRs, and/or any suitable entity. In variations, user profiles can be updated with correlations generated over time in order to determine historical trends, compare data (e.g., blood pressure waveforms generated as in Block S150, etc.) over extended time periods (e.g., over months, years, etc.), to compare data to other users, and/or to perform any relevant analysis in relation to data tracked over time.

However, generating a correlation S120 can be performed in any suitable manner.

3.2.A Providing a Push Pulse.

Block S120 can additionally or alternatively include Block S122, which recites providing a push pulse. Block S122 functions to provide a pushing force for perturbation of a target vessel, which induces a measurable response in the target vessel that can be used to determine one or more cardiovascular parameters.

In relation to Block S122, providing a push pulse preferably provides a compressing force at a target region (e.g., proximal a vessel of the user), thereby displacing tissue (e.g., effecting a temporary deflection in vessel wall position) and/or generating propagating shear waves. However, provided push pulses can provide any suitable type of force for perturbing objects associated with a target region. A push pulse is preferably characterized by one or more push pulse parameters (e.g., a push pulse parameter of a set of push pulse parameters as in Block S120). Any number of push pulses can be provided, where each push pulse of a series of push pulses can be characterized by the same or different push pulse parameters as other push pulses in the series of push pulses. However, providing one or more push pulses can engender any suitable effect on a vessel and/or suitable regions of a user.

With respect to Block S122, providing a push pulse can include manifesting a push pulse at a target region (e.g., of a user). Push pulses are preferably manifested, arranged, located at, and/or positioned proximal a vessel (e.g., a blood vessel), of a user, but can additionally or alternatively be adjacent, distant, near, far, above, below, within, and/or have any suitable positional relationship relative a vessel and/or other suitable body region of a user. In an example, providing a push pulse includes providing a push pulse at the outer surface of a vessel wall. In another example, provided push pulses can manifest at a region prior to reaching a vessel wall in relation to an ultrasound energy transmission path. In a further example, provided push pulses can manifest within bounds of a vessel wall. Manifested push pulses can have any suitable range of effects. For example, compressive forces induced by a push pulse manifested at the vessel wall outer surface can extend any suitable distance along the longitudinal axis of the vessel wall. However, push pulses can be provided, manifest, and/or affect any other suitable region of a vessel.

Regarding temporal characteristics relating to Block S122, any number of push pulses can be provided within and/or associated with a temporal indicator (e.g., within a sampling time period, within a time window, etc.), but can additionally and/or alternatively be characterized by non-temporal indicators (e.g., associating a number of push pulses with a defined volume, etc.). Providing a push pulse S122 is preferably in response to a manually or automatically determined trigger (e.g., as described in Section 3.2), but can otherwise be performed at any suitable time. Providing push pulses S122 is preferably characterized by temporal preferences for sampling. Temporal preferences for sampling can include: sampling frequency, time of sampling, time between samples (e.g., time between voltage steps), and/or any other suitable temporal preferences. Temporal preferences can be manually established (e.g., by a user, by a researcher, by a care provider, etc.), automatically established (e.g., according to a machine learning model and/or other suitable model) and/or otherwise determined. In variations, the boundaries of the sampling interval are preferably in compliance with Nyquist sampling criteria for pressure waveform frequency bandwidth. In an example, the sampling time period is shorter than a reference time period corresponding to a duration for a pressure of the vessel to change by a predetermined target accuracy percent. In a specific example, for a target 1% pressure accuracy, data points for a single correlation between push pulse parameters (e.g., a set of push pulse voltages) and push pulse-dependent values (e.g., a set of vessel displacement measurements) are collected in a shorter duration than the duration required for a vessel pressure to change by 1%. In another specific example, for a user with a pulse rate of 180 beats/minute, and a blood pressure of 180/80 mmHg, the user has a waveform bandwidth of approximately 18 Hz and a max slew rate of 11310 mmHg/s. For a target blood pressure accuracy of <5 mmHg, dividing the target accuracy by the slew rate gives a target sampling window of <442 μs. From the target sampling window and the amounts of time for push pulse transmission, receipt by a detector, and/or imaging, a number of potential push pulse samples fitting within the target sampling window can be determined. However, providing a push pulse can be performed at any suitable time in compliance with any suitable conditions.

In a variation of Block S122, providing a push pulse can include providing a series of push pulses characterized by a predetermined order. A predetermined order for push pulse provision is preferably an order of push pulse parameters to use in providing push pulses. For example, providing a push pulse according to a predetermined order can include: determining a sequence of administering a set of push pulse parameters for series of push pulses, and providing the series of push pulses in an order based on the determined sequence. A set of push pulses can be provided with push pulse parameters ordered by category and/or value (e.g., by voltage, by pressure) in an increasing, decreasing, alternating, and/or any suitable manner.

Figure 3A:
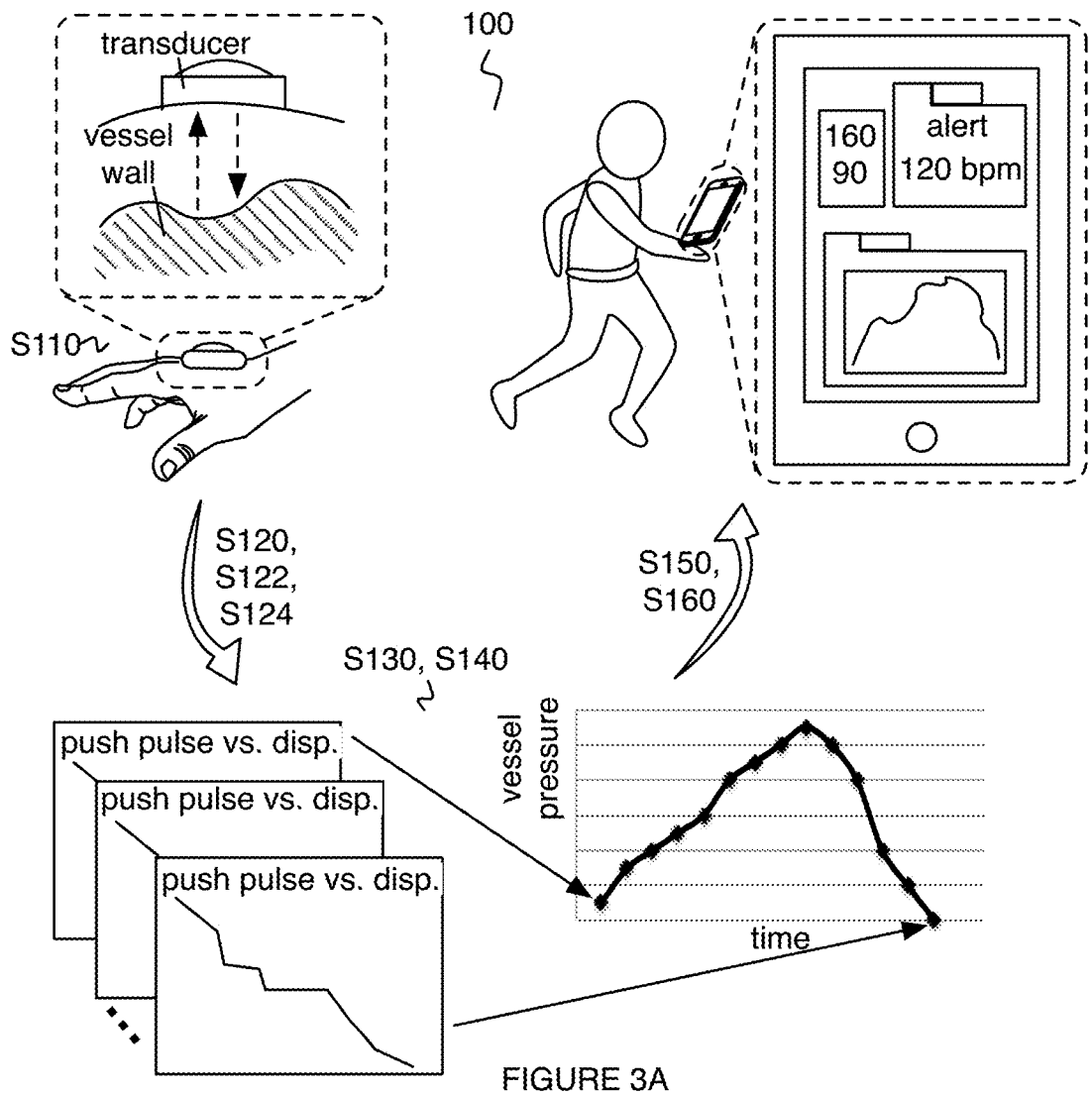
Figure 3B:
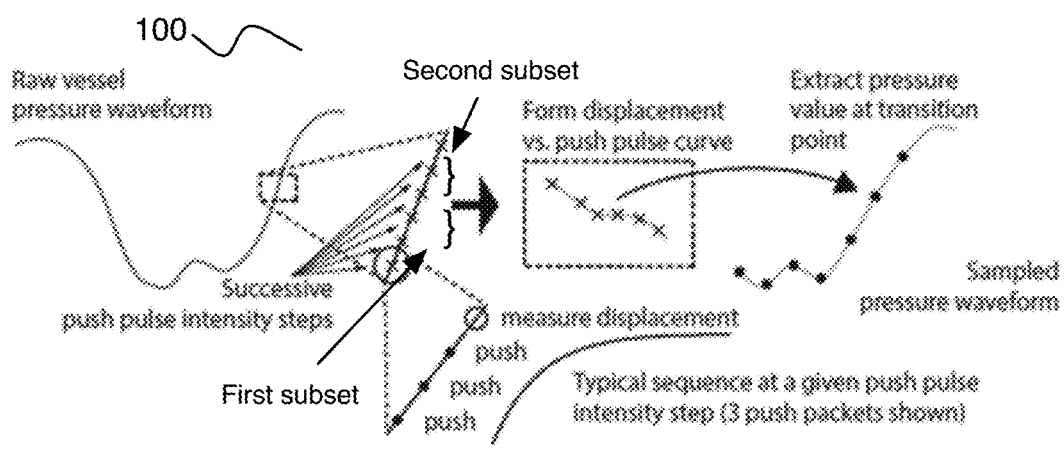

As shown in FIG. 3B, in an example, a set of push pulse parameters can include a first subset of the set of push pulse pressure parameters, each push pulse pressure parameter of the first subset below a pressure in a vessel (e.g., a blood vessel) at the sampling time period, and a second subset of the set of push pulse pressure parameters, each push pulse pressure parameter of the second subset above the pressure in the vessel at the sampling time period. In this example, the ultrasound system can emit acoustic energy with the push pulse, including providing each push pulse characterized by the first subset of push pulse pressure parameters prior to providing each push pulse characterized by the second subset of push pulse pressure parameters (e.g., providing push pulses according to an increasing order of push pulse parameters). In another example, a series of provided push pulses can be characterized by alternating low and high pressures, thereby preferably mitigating hysteresis effects in associated media. For examples of providing push pulses according to a sequence of push pulse pressures, the increment value between value-adjacent push pulse pressure parameters is preferably half a desired final measurement resolution. In a specific example, each push pulse parameter of the set of push pulse parameters is stepwise incremented relative a preceding push pulse parameter, wherein the stepwise increment is characterized by an increment value approximately half a final measurement resolution value. In other examples, providing a set of push pulses includes providing a set of push pulses characterized by an automatically determined order (e.g., using a machine learning model and/or any other suitable model). However, providing push pulses in a specified order can be otherwise performed.

Figure 4:
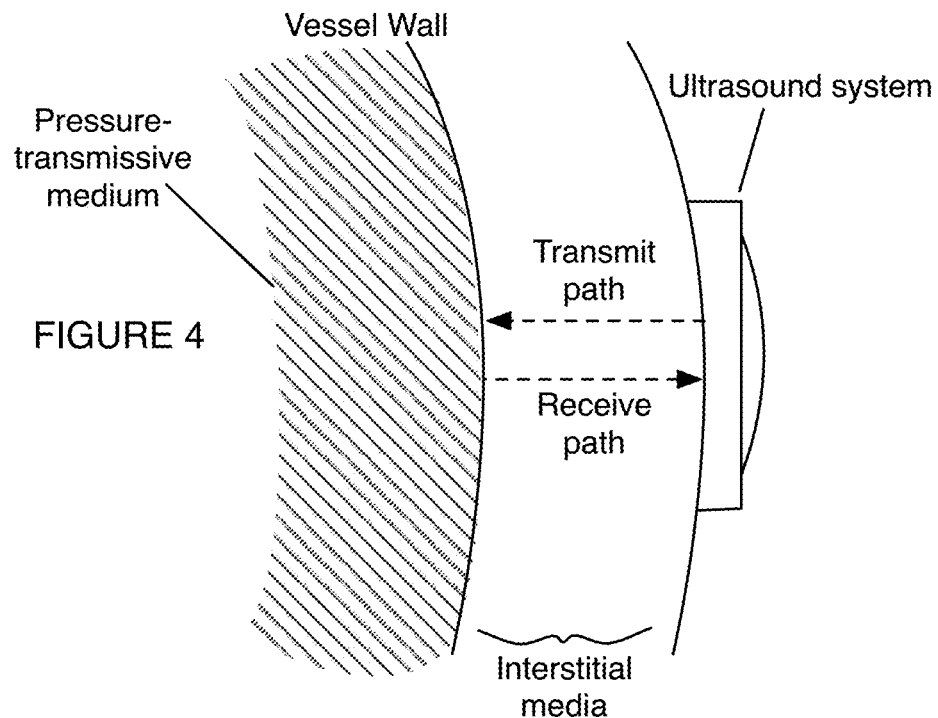
FIGS. 4-6 depict schematic representations of examples of using an ultrasound system to provide push pulses.

As shown in FIG. 4, in another variation of Block S122, providing a push pulse can including emitting acoustic energy with a push pulse. Acoustic energy is preferably emitted from an ultrasound transducer of the ultrasound system, but can additionally or alternatively produced by any suitable component of the ultrasound system and/or other system. Emitted acoustic energy preferably travels along a transmit path, from which a push pulse can manifest. A transmit path axis preferably intersects and is approximately perpendicular an interface plane between an ultrasound transducer and the exterior surface of a body region of the user. Additionally or alternatively, a transmit path axis is preferably approximately perpendicular a longitudinal axis of vessel (e.g., a blood vessel). However, a ultrasound transmit path can be perpendicular, parallel, angled and/or have any suitable orientation in relation to axes, planes, and/or other points of reference of any suitable region. Emitted acoustic energy can have any suitable beam shape, (e.g., planar, diverging, etc.), frequency, amplitude, duration, and/or any suitable energy characteristic. However, emitting acoustic energy with a push pulse can be performed in any suitable manner.

In another variation, providing a push pulse can include adjusting a transmission direction of an ultrasound transducer. Adjusting the transmission direction preferably includes adjusting the transmission direction of acoustic energy, thereby modifying the corresponding transmit path, but can additionally or alternatively include adjusting the transmission direction of any suitable entity. In this variation, the ultrasound system can include an ultrasound transducer and an electronics subsystem configured to adjust a transmission direction for an array of transmitter elements of the transducer. For example, providing the push pulse can include adjusting the transmission direction towards the vessel for an array of transmitter elements of a transducer patch, and providing the push pulse based on the transmission direction. Additionally or alternatively adjusting a transmission direction can include embodiments, variations, examples and/or any elements described in U.S. application Ser. No. 13/655,191 entitled "System and Method for Unattended Monitoring of Blood Flow," filed 18 Oct. 2012, which is herein incorporated in its entirety by this reference. However, adjusting the transmission direction for providing push pulses can be performed in any suitable fashion.

Additionally or alternatively, providing a push pulse can be performed in any suitable fashion.

3.2.B Determining a Push Pulse-Dependent Value.

Block S120 can additionally or alternatively include Block S124, which recites: determining a push pulse-dependent value. Block S124 functions to measure values dependent on push pulses provided as in S124, in order to evaluate cardiovascular parameters as in Blocks S130, S140, S150, and/or other portions of the method 100. As described above, push pulse-dependent parameters can include one or more of: vessel morphological aspects, mechanical properties, vessel fluid aspects, physical properties and any other suitable push pulse-dependent parameter. In a specific example, Block S124 can include determining a displacement value based on axial displacement (e.g., parallel a transmit path of an ultrasound transducer) of the blood vessel by the push pulse, wherein a set of displacement values (e.g., a set of displacement values correlated with a set of push pulse parameters as in Block S120) comprises the displacement value. However, Block S124 can include determining any suitable push pulse-dependent value.

In relation to Block S124, determining a push pulse-dependent value is preferably based on one or more parameters of the push pulse (e.g., push pulse parameters, push pulse effects, etc.), but can additionally or alternatively be based on, determined by, and/or derived from environmental conditions (e.g., temperature, time of day, etc.), target vessel characteristics, and/or any other suitable criteria. Push pulse-dependent parameters (e.g., axial displacement) are preferably measured by a transducer used in providing a push pulse as in Block S122, but can additionally or alternatively be measured using an additional transducer (e.g., positioned at an adjacent location, at an opposing location, etc.), and/or any other suitable component. In a specific example, depth of deflection is preferably measured with an additional ultrasonic pulse-echo-style measurement along a same transmit-receive path as the path for acoustic energy emission by the ultrasound transducer, but can additionally or alternatively be measured along a different path. In variations leveraging multiple transducers and/or components to determine push pulse-dependent values, the multiple transducers and/or components preferably have overlapping fields of view, but can alternatively have non-overlapping fields of view. However, any other suitable component(s) can be utilized in determining push pulse-dependent values.

Regarding Block S124, determining a push pulse-dependent value preferably includes using Speckle-tracking to measure a push pulse-dependent value (e.g., displacement). In more detail, Block S124 can include implementing speckle-tracking to obtain a naturally occurring speckle pattern of a region of interest over time, in order to analyze and image the motion of tissues in the body. Speckle-tracking can, however, be used to perform any other suitable relevant operations. Additionally or alternatively, techniques for measuring push pulse-dependent values can include one or more of Doppler ultrasonic velocity measurements, optical methods (e.g., photoacoustic methods), back-echo measurements, transmitted echo measurements, and/or any other suitable methods. In a specific example, Block S124 can include tracking vessel displacement in b-mode ultrasound images (e.g., using Speckle-tracking) in response to a provided push pulse, to acquire micron-level displacement resolution. However, any suitable technique can be used for determining push pulse-dependent parameters.

Additionally or alternatively, determining a push pulse-dependent value can be performed in any suitable fashion.

3.3 Generating an Attribute Value Associated with the Vessel.

Block S130 recites: generating an attribute value associated with the vessel, which functions to determine a value associated with a characteristic (e.g., internal pressure) of a target vessel using data generated in at least one of Blocks S120, S122, and S124. A generated attribute value is preferably an instantaneous internal pressure value from the target vessel (e.g., an internal pressure at the region of the target vessel at which a local push pulse was provided as in Block S122). Pressure values can be described with units including: mmHg, Pa, pounds per square inch, bar, grams-force, and/or any suitable units. Additionally or alternatively, generated attribute value types can include additional pressure characteristics (e.g., external vessel pressure, internal vessel pressure at different regions of the target vessel, nearby interstitial media pressure, etc.), any suitable characteristic described above in Section 3.2 in relation to push pulse-dependent values (e.g., vessel morphological aspects, mechanical properties, vessel fluid aspects, physical properties, etc.), and/or any other suitable attribute value. Generated attribute values are preferably associated with the target vessel (e.g., a vessel upon which emitted acoustic energy is directed from an ultrasound transducer coupled to a body region of the user), but can additionally or alternatively be associated with any suitable body region of the user. However, attribute values generated as in S130 can possess and/or describe any suitable property of a target vessel, nearby media, and/or any other related physiological entity.

Regarding temporal characteristics relating to Block S130, generated attribute values (e.g. determined based on a correlation generated as in Block S120) preferably correspond to a sampling time period associated with the constituents (e.g., a correlation) from which the attribute values are generated. Additionally or alternatively generated attribute values can be associated with and/or correspond to any suitable temporal indicator. Generating an attribute value S130 is preferably performed in response to generating a correlation as in Block S120, but can additionally and/or alternatively be performed at any suitable time. For example, a set of attribute values can be generated in response to generation of a set of correlations, thereby aggregating similar types of computational operations (e.g., through use of parallel computing principles and improving the functioning of the computer itself). However, generating attribute values S130 can possess any suitable temporal characteristics.

In relation to Block S130, generating an attribute value is preferably based on a correlation generated as in Block S120. For example, Block S130 can include generating a pressure value from the vessel based on the correlation between a set of push pulse parameters and a set of push pulse-dependent values. In another example, Block S130 can include generating a blood pressure value from a blood vessel based on a set of push pulse voltage parameters and a set of vessel displacement values measured in response to provided push pulses characterized by the set of push pulse voltage parameters. Additionally or alternatively, generating an attribute value can be based on previously generated attribute values, data generated as in Blocks S120, S122, S124, and/or any other portion of the method 100, supplemental information (e.g., patient demographic information, patient behavioral information, electronic health records, etc.), and/or any other suitable information. However, generating an attribute value can be determined from and/or based on any suitable data.

As shown in FIGS. 7B-7C, 8A-8B, and 9, in a variation of Block S130, generating an attribute value can be based on a transition region of a correlation determined as in Block S120. One or more transition regions are preferably included in a correlation between push pulse parameters and vessel displacement (e.g., axial vessel displacement) in response to provided push pulses characterized by the push pulse parameters, but any suitable correlation can include any number of transition regions. In an example, Block S130 can include generating a blood pressure value from the blood vessel based on a transition region in the correlation between the set of push pulse pressure parameters and the set of displacement values. In Block S130, transition regions preferably describe a region of approximately constant push pulse-dependent values as push pulse parameters are varied.

In a specific example of Block S130, a series of provided push pulses is characterized by a set of push pulse pressures including push pulse pressures below, approximately at, and above an internal fluid pressure of a target vessel. For push pulse pressure below the internal vessel pressure, the vessel wall preferably displaces modestly as compressive forces relieve circumferential wall tension. For push pulse pressures approximately equal to the internal vessel pressure, vessel wall tension and push pressure balance internal vessel pressure. For such pressures, vessel displacement preferably remains approximately stable. For push pulse pressure above an internal fluid pressure, a pushed vessel region preferably transitions to shear stress with neighboring unpushed wall material, and equilibrium is preferably reached when shear tension balances the push forces. Additionally or alternatively, characteristics described above can correspond to transition points, transition areas, transition, transition time periods, and/or any other suitable transition indicator. As shown in FIGS. 7A-7C, in examples where push pulses are characterized by a set of push pulse voltages, a transition region can correspond to and/or be associated with a knee voltage, which can describe a push pulse voltage at which the push pulse pressure and internal vessel pressure are approximately equal. However, transition regions can be defined in any suitable manner.

In relation to this variation of Block S130, transition regions preferably correspond to a time window of a sampling time period associated with a correlation between a set of push pulse parameters and push pulse-dependent values. In a specific example, generating a pressure value includes identifying a transition push pulse parameter of the set of push pulse parameters, wherein the transition push pulse parameter corresponds to a time window of the sampling time period, and wherein a pressure of the push pulse is substantially equal to a pressure in the vessel at the time window. In another specific example, the transition region can correspond to a time window of the time period and can include a transition push pulse pressure parameter of the set of push pulse pressure parameters, wherein the transition push pulse parameter directly corresponds to a pressure in the blood vessel associated with the time window. In this specific example, the transition push pulse pressure parameter can be substantially equal to the pressure in the blood vessel at the time window. In this specific example, the transition push pulse pressure parameter can additionally or alternatively differ from the pressure in the blood vessel by approximately a known pressure delta (and/or range of pressure deltas) at the time window, the known pressure delta associated with one or more medium aspects (e.g., one or more physical properties of a medium) proximal the blood vessel. In this specific example, the pressure deltas can correlate with hysteresis in the location of the transition region, the hysteresis caused by the history of the vessel and/or push pulse pressures experienced during measurement. However, transition regions can correspond with any suitable temporal indicator associated with any suitable phenomena.

Figure 8A:
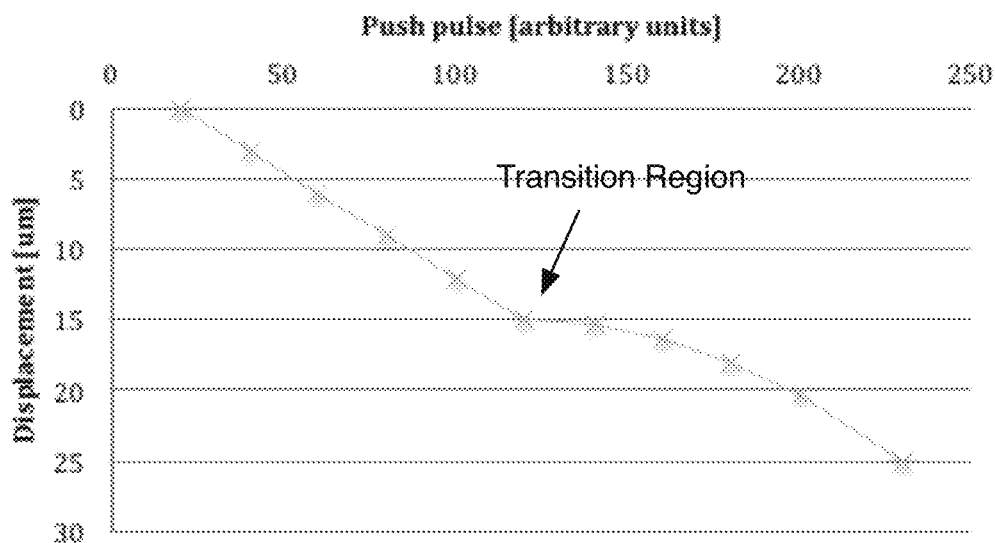
FIGS. 8A-8B, 9, and 10 depict graphical representations of generated correlations.
Figure 8B:
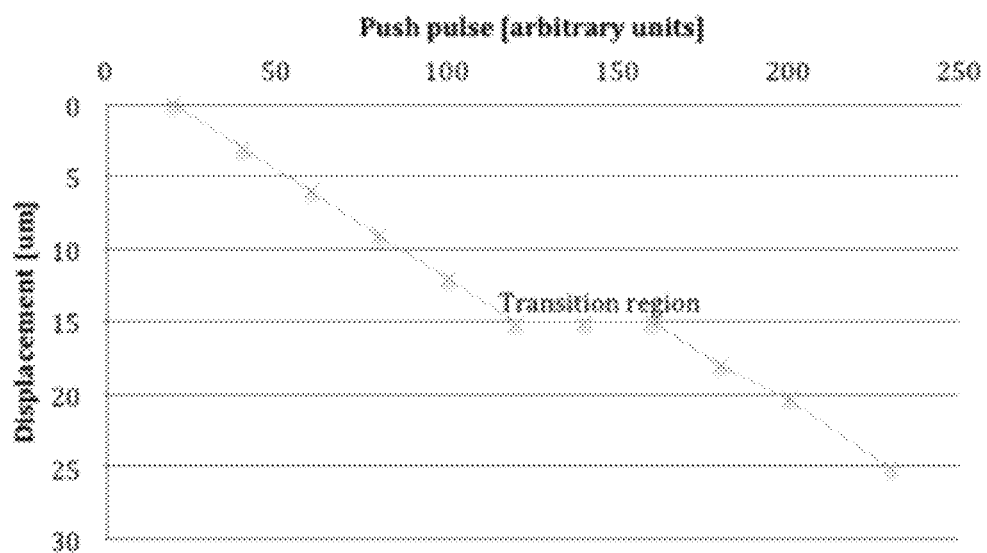

Related to this variation of Block S130, transition regions can be described as a single transition point (e.g., as shown in FIG. 8A), as multiple transition points (e.g., as shown in FIG. 8B), but can additionally or alternatively be described in any suitable manner. Transition region characteristics (e.g., number of data points in the transition region, temporal indicators associated with the transition region, shape of transition region, shape of curve segments flanking a transition region, etc.) can be influenced by, be determined from, and/or be based on vessel wall properties, nearby media properties, and/or any other suitable information. As shown in FIGS. 7A-7B, 8A-8B, and 9, for a correlation curve including a transition region, the transition region is preferably flanked by two different segments of the correlation curve. The two different segments preferably correspond with two different physical phenomena of vessel wall deflection, determined by polarity of differential pressure (e.g., applied push pulse minus instantaneous internal vessel pressure) across the vessel wall. However, transition regions and/or regions surrounding transition regions can be described in any suitable manner.

Figure 9:
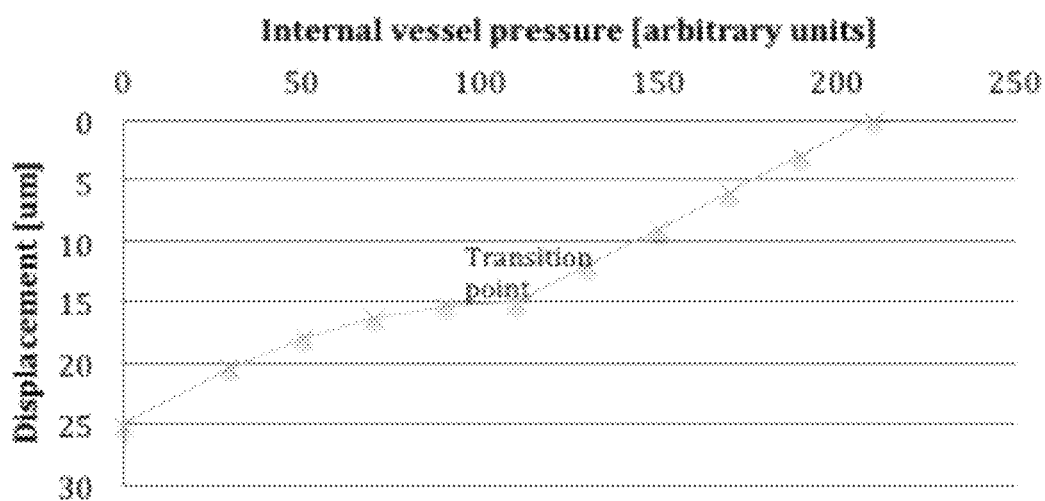

As shown in FIG. 9, in another variation related to Block S130, the method 100 can include generating a measurement of an attribute value based on a single push pulse-dependent value and a correlation between push pulse dependent-values and attribute values. In this variation, data from a plurality of correlations between sets of push pulse parameters and push pulse-dependent values can be leveraged in generating multiple attribute values, from which an attribute value correlation between the attribute values and push pulse-dependent values can be generated. In combining data from a plurality of correlations to generate an attribute value correlation, averaging algorithms and/or any other suitable algorithms can be used in determining final measured pressure. Additionally or alternatively, selection algorithms can be used for selecting, based on confidence level, attribute value correlations and/or correlations between push pulse parameters and push pulse-dependent values. However, any suitable algorithms can be used. One or more attribute value correlations between attribute values and push pulse-dependent values can be used in extrapolating and/or interpolating attribute values from subsequently measured push pulse-dependent values (e.g., a single measured push pulse-dependent values can be used in inferring an attribute value). Additionally or alternatively, attribute value correlations can be used in generating an attribute value waveform as in Block S140, for determining an unknown push pulse-dependent value from a measured attribute value, and/or for any other suitable purpose.

In a specific example of this variation of Block S130, the method 100 can include generating a vessel pressure correlation between (1) the internal vessel pressure value and the set of supplemental internal vessel pressure values, and (2) corresponding push pulse-dependent values; determining a subsequent push pulse-dependent value at a later time period subsequent the sampling time period and the set of time periods corresponding to the set of supplemental internal vessel pressure values; and determining an estimated pressure value of the vessel corresponding to the later time period, based on the subsequent push pulse-dependent value and the vessel pressure correlation. However, generating a measurement of an attribute value based on an attribute value correlation can be performed in any suitable manner.

Figure 10:
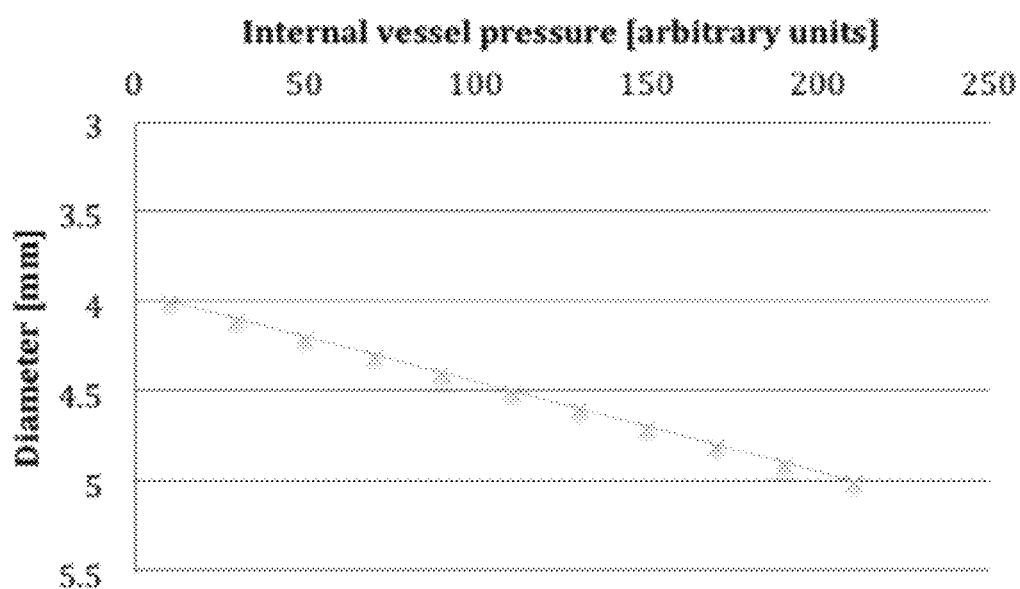

As shown in FIG. 10, in another variation related to Block S130, the method 100 can include determining an attribute value based on a generated correlation between target vessel diameters and vessel attribute values (e.g., internal vessel pressures). In this variation, a measured vessel diameter corresponding to a time period can be used with the generated correlation in order to determine a vessel attribute value corresponding to the time period, which can thereby circumvent the need for additional push pulse-based measurements. In this variation, a diameter value for a target vessel can be measured contemporaneously, in parallel with, simultaneously, and/or with any suitable temporal relationship with measuring push pulse-dependent values as in Block S124. As such, a given diameter value is preferably associated with a time period (e.g., a sampling time period) corresponding to a generated attribute value (e.g., an internal vessel pressure), but can be associated with any suitable temporal indicator. In a specific example, Block S130 can include generating a set of vessel diameter measurements of the blood vessel, including: measuring a vessel diameter corresponding to the sampling time period (e.g., associated with providing a set of push pulses characterized by set of push pulse parameters), the set of vessel diameter measurements including the vessel diameter, and measuring a set of supplemental vessel diameters, each corresponding to a distinct time period of the set of time periods, the set of vessel diameter measurements including the set of supplemental vessel diameters; and generating a correlation between the set of vessel diameter measurements and a set of blood pressure values comprising the blood pressure value and the set of supplemental blood pressure values. In this specific example, the method 100 can additionally or alternatively include: measuring a subsequent vessel diameter at a later time period subsequent the sampling time period and the set of time periods; and determining an estimated blood pressure value corresponding to the later time period, based on the subsequent vessel diameter and the correlation between the set of vessel diameter measurements and the set of blood pressure values.

In another variation of Block S130, determining an attribute value can include updating a correlation generated as in Block S120, and generating an attribute value based on the updated correlation. Updated correlations are preferably based on updated push pulse dependent values (e.g., more recent values, values with higher confidence levels, etc.), updated supplemental measurements (e.g., updated user information, updated vessel diameter measurements, etc.) but can be based on any suitable information. In a specific example, the method 100 can include generating an updated correlation between an updated set of vessel diameter measurements and an updated set of blood pressure values, the updated correlation associated with a set of updated time periods subsequent the sampling time period and the set of time periods corresponding to a supplemental set of blood pressure values; and determining an updated estimated blood pressure value based on the subsequent vessel diameter and the updated correlation, wherein the updated estimated blood pressure value is distinct from an initial estimated blood pressure value determined based on an initial correlation between the set of initial vessel diameter measurements and the set of initial blood pressure values. However, updating a correlation can be performed in any suitable manner.

In another variation of Block S130, curve profile templates can be applied to sets of data (e.g., a set of push pulse parameters and a set of a push pulse-dependent values) in generating a correlation and/or improving a resolution of a transition region, thereby improving accuracy for determining an attribute value (e.g., internal vessel pressure). Curve profile templates can be generated from previously generated correlation curves, manually generated curve profile templates (e.g., with data points curated by a researcher, a care provider, etc.), automatically generated curve profile templates (e.g., a composite reference curve profile template generated from combination of multiple curve profiles, etc.), and/or from any suitable constituents. However, generating and/or applying a curve profile template can be performed in any suitable manner.

3.4 Generating an Attribute Value Waveform.

Block S140 recites: generating an attribute value waveform, which functions to determine a curve describing a time-varying behavior of an attribute value (e.g., an internal vessel pressure). Waveforms are preferably generated for an attribute value type described in relation to Block S130, but can be generated for push pulse-dependent value measured as in Block S124, and/or any suitable data relating to any portion of the method 100. Waveforms are preferably time-varying but can vary and/or be dependent upon any suitable variable (e.g., varying with respect to a push pulse parameter type such as pressure, voltage, etc.). Examples of waveforms can include waveforms of one or more pressure characteristics (e.g., blood pressure, instantaneous internal vessel pressure, etc.), waveforms of one or more flow characteristics (e.g., flow velocity, flow direction, etc.), waveforms of one or more morphological aspects (e.g., vessel wall displacement, etc.), and/or any other suitable waveform types. Generated waveforms preferably describe relative measurements (e.g., of an attribute value type), but can additionally or alternatively describe absolute measurements. However, generated attribute value waveforms can possess any suitable property.

In relation to Block S140, generated attribute value waveforms are preferably generated from a generated attribute value as in Block S130, and a set of supplemental attribute values. In variations, the supplemental attribute values can include one or more of: pressure values (e.g., instantaneous internal vessel pressure, external vessel pressure, etc.), conventional ultrasound values (e.g., from a Doppler and/or speckle-tracked flow ultrasound scan for providing blood flow metrics in addition or alternative to blood pressure values), and/or any suitable characteristic described above in Sections 3.2 and/or 3.3 in relation to push pulse-dependent values and/or attribute values (e.g., vessel morphological aspects, mechanical properties, vessel fluid aspects, physical properties, etc.), and/or any other suitable attribute value. The set of supplemental attribute values preferably correspond to a set of time periods (e.g., in a 1 attribute value-to-1 time period relationship or any suitable numerical relationship), where the set of time periods are preferably distinct (e.g., non-identical) from the sampling time period. Additionally or alternatively, the set of time periods corresponding to a set of supplemental attribute values can have overlapping sections with the sampling time period, but can otherwise be completely non-overlapping and/or have any suitable relationship with the sampling time period. In a specific example, Block S140 can include generating a time-varying blood pressure waveform from the blood pressure value (e.g., generated as in Block S130) and a set of supplemental blood pressure values corresponding to a set of time periods distinct from the sampling time period. In this specific example, systolic and diastolic blood pressure values can be determined based on the blood pressure waveform, such as through max/min thresholding on an upsampled noise-filtered signal. However, generated attribute value waveforms can be used in any suitable manner for evaluating cardiovascular health.

In a variation of Block S140, a set of supplemental attribute values are generated according to operations relating to Blocks S110, S120, S122, S124, S130, and/or other portions of the method 100. For example, generating a supplemental attribute values can include generating a set of supplementary correlations, including for each time period of the set of time periods: generating a supplementary correlation between a set of supplementary push pulse parameters and a set of supplemental push pulse-dependent values associated with the vessel, wherein the set of supplementary correlations includes the supplementary correlation, and wherein generating the correlation comprises for each supplementary push pulse parameter of the set of supplementary push pulse parameters: providing a supplementary push pulse with the ultrasound system, the supplementary push pulse characterized by the supplementary push pulse parameter, and determining a supplemental push pulse-dependent value based on the push pulse, the set of supplementary push pulse-dependent values comprising the supplementary push pulse-dependent value; and generating a supplemental pressure value based on the correlation between the set of supplementary push pulse parameters and the set of supplemental push pulse-dependent values, wherein the set of supplemental pressure values comprises the supplemental pressure value. Additionally or alternatively, supplemental attribute values can be collected from third party sources (e.g., electronic health records, blood pressure monitoring data derived from other medical devices, patient databases, etc.), a user (e.g., user-provided attribute values such as through a digitally presented survey), and/or any other suitable source. However, generating and/or processing supplemental attribute values for generating attribute value waveforms can be performed in any suitable manner. Additionally or alternatively, attribute value waveforms can be generated from, based on, and/or determined by any suitable information related to portions of the method 100.

With respect to temporal aspects of Block S140, generating one or more attribute value waveforms can be performed in response to a manual trigger (e.g., triggered by a user request for a cardiovascular health analysis, by a care provider request, by a researcher request, etc.), an automatic trigger (e.g., based on established conditions, preferences, rules, models, etc.), at specified time intervals (e.g., for every minute, hour, day, week, month, year, etc.), and/or any suitable criteria. Generating one or more attribute value waveforms is preferably in response to generating an attribute value as in Block S130, but can be performed at any suitable time in relation to portions of the method 100, and/or at any suitable time.

In relation to Block S140, as shown in FIG. 1, portions of generating an attribute value waveform can be performed at a processing subsystem (e.g., a processing subsystem used for generating an attribute value as in Block S130) of an ultrasound system, a remote server, and/or any other suitable component.

In a variation of Block S140, generating an attribute value waveform can include performing processing operations on push pulse-dependent values, generated attribute values, supplementary attribute values, waveforms, and/or other suitable data relevant to the method 100. Processing operations can include: normalization, filtering, noise reduction, smoothing, model fitting, transformations, mathematical operations (e.g., derivatives, moving averages, etc.), image processing, and/or any other suitable processing technique. Additionally or alternatively, the method 100 can include generating an analysis of an attribute value waveform; and identifying one or more cardiovascular conditions (e.g., defective heart valve, heart failure, etc.) based on the analysis. In a specific example, generating an attribute value waveform can include normalizing a waveform to an amplitude measured for a reference profile (e.g., a baseline physiological profile such as a blood pressure profile of 120 mmHg systolic and 80 mmHg diastolic. Additionally or alternatively, performing processing operations in generating an attribute value waveform can be performed in any suitable fashion.

However, generating an attribute value waveform can be performed in any suitable manner.

3.5 Determining an Absolute Value of an Attribute Value.

The method 100 can additionally or alternatively include Block S150, which recites: determining an absolute value of an attribute value. Block S150 functions to determine an absolute metric (e.g., as opposed to a relative metric) for an attribute value (e.g., generated as in Block S130), which can be used in generating an absolute value version of a generated waveform (e.g., generated as in Block S140). Absolute values are preferably generated for pressure attribute values (e.g., a blood pressure from a blood vessel), but can be generated for any suitable attribute value type. Generating an absolute value of an attribute value preferably includes quantitatively characterizing (e.g., characterizing an absolute pressure applied by the push pulse, a push pulse intensity at the vessel wall, etc.) one or more push pulses provided as in Block S122, where the absolute value of the attribute value can be derived from the quantitative characterization of the one or more push pulses. Additionally or alternatively, generating an absolute attribute value can be determine by, derived from, and/or based upon any suitable data.

With respect to Block S150, determining an absolute attribute value can be performed in response to generating an attribute value, in response to generating an attribute value waveform, but can additionally or alternatively have any suitable temporal relationship with portions of the method 100, and/or can be performed at any suitable time. Generating an absolute value of an attribute value is preferably performed at the same processing system used in performing Block S130, but portions of Block S150 can be performed by any suitable processing system (e.g., processing subsystem of an ultrasound system, user device, remote server, care provider device, etc.).

Figure 14:
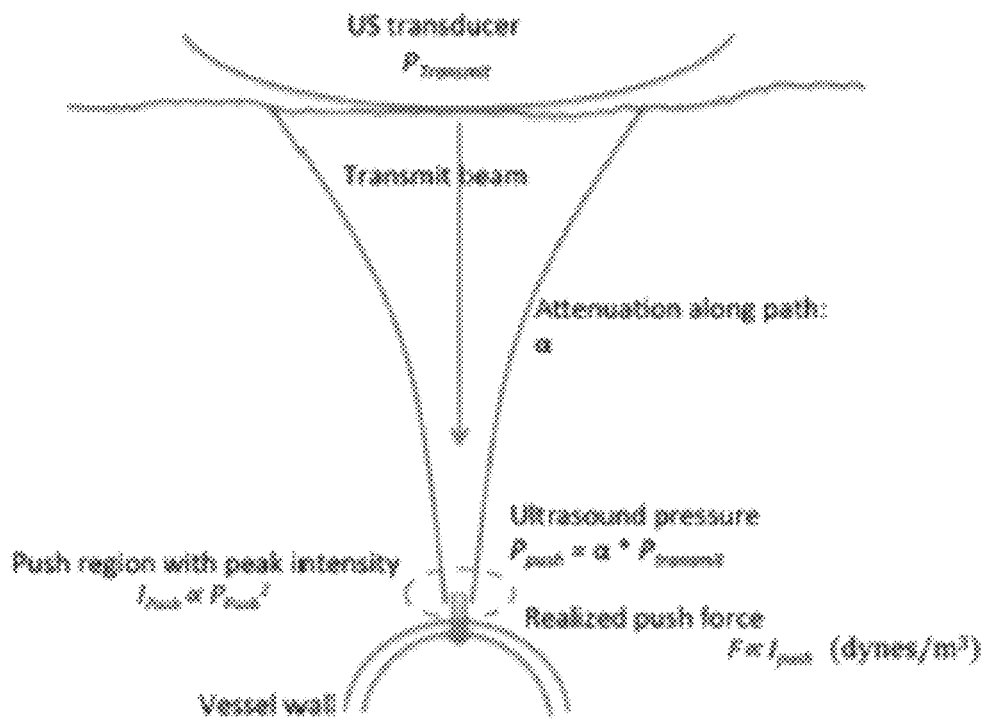
FIGS. 14-15 depict schematic representations of examples of using an ultrasound system to provide push pulses.
Figure 15:
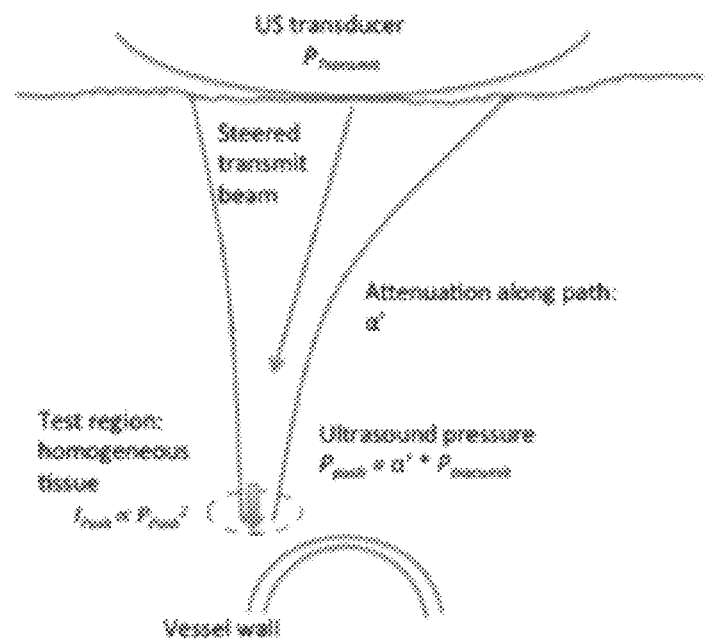

As shown in FIGS. 14 and 15, in a variation of Block S150, determining an absolute attribute value can be based on any one or more of the following relationships:

$$P_{push} \propto \alpha * P_{Transmit} * G_F$$

$$I_{push} \propto P_{Push}^2 * G_F$$

$$F \propto I_{push}$$

where $\alpha$ is an attenuation coefficient describing attenuation along a transmit and/or return propagation path from the ultrasound system, $P_{transmit}$ is a known push pulse power parameter associated with transmission of the push pulse by the ultrasound system, $G_F$ is a focal gain associated with the push pulse, $I_{push}$ is an acoustic intensity at a push region characterized by $P_{push}$, which is a mechanical push parameter manifested proximal a vessel wall, and F is the push force realized for the duration of the push pulse. In this variation, determining the absolute attribute value can include identifying a transition region (e.g., as described above with respect to Block S130) in a tube wall displacement vs. transducer voltage curve, where the transition region includes a push transmit voltage that equilibrates with tube pressure. The push transmit voltage can subsequently be converted to a localized ultrasound intensity. In an example, the push transmit voltage-to-intensity conversion can include measuring a displacement of a region of homogenous tissue (e.g., muscle) to a side of the blood vessel and at the same depth; and estimating a field intensity based on an a priori known deflection vs. intensity profile for the tissue type. In this example, path losses can be assumed to be the same for the test region and the vessel wall. In another example, the push transmit voltage-to-intensity conversion can include measuring the echo of a push pulse from the vessel wall and back-calculating attenuation loss. In this example, attenuation and focal gain/loss can be assumed to be the same in the transmit and return directions, and an $\alpha$ priori knowledge of a backscatter efficiency $\beta$ from the vessel wall can be used. In another example, the push transmit voltage-to-intensity conversion can include measuring $P_{return}$ at multiple $P_{transmit}$ frequencies when $\alpha$ and/or $\beta$ have frequency dependence; and solving the resulting system of equations for $\alpha$ and $\beta$. Subsequent to the push transmit voltage-to-intensity conversion, Block S150 can include converting the localized ultrasound intensity to an applied pressure on the tube wall, where the ultrasound energy generates a localized push in tissue at the focal point of the transducer. Given that attenuation, scatter, and specular reflection contribute to the energy conversion process, conversion factors can vary between patients. As such, the method 100 can include calibrating for different patients through generating a parametrically-driven conversion factor equation (e.g., for accounting for variations in tissue between patients) from patient data (e.g., from a plurality of patients) including known systolic and/or diastolic blood pressures (e.g., using an external cuff and/or arterial line) correlated to estimated localized ultrasound intensities at corresponding transition regions, B-mode ultrasound images characterizing tissue at focal points, and/or any suitable data.

Figure 6:
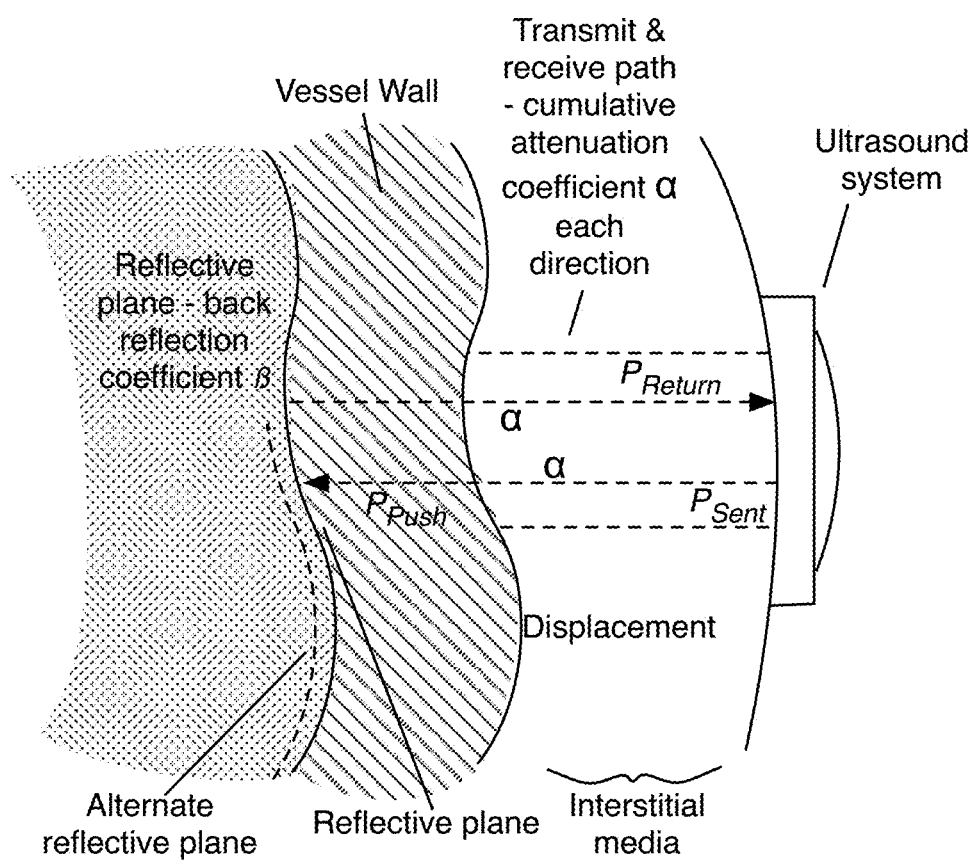

As shown in FIG. 6, in another variation of Block S150, determining an absolute attribute value can be based on an ultrasound backscattering coefficient $\beta$ for a known interface or material (e.g., flowing blood with a given hematocrit). In a specific example, an absolute value of a push pulse pressure can be determined by:

$$P_{return} = P_{push} * \beta * \alpha$$

$$P_{push} = P_{sent} * \alpha$$

Thus: $P_{push} = \sqrt{(P_{return} * P_{sent})/\beta}$ where $\alpha$ is an attenuation coefficient describing attenuation along a transmit and/or return propagation path from the ultrasound system, $P_{sent}$ is a known push pulse power parameter associated with transmission of the push pulse by the ultrasound system, $P_{return}$ is a reflected push pulse parameter measured at the ultrasound system, and $P_{push}$ is a mechanical push parameter manifested proximal a vessel wall, with back-reflection from a reflective plane with backscatter efficiency $\beta$. Backscatter efficiency $\beta$ can be time-varying and influenced by flow velocity, hematocrit concentration, rouleaux formation, and/or other suitable conditions. In particular, instantaneous values of backscatter efficiency $\beta$ are preferably parametrically determinable from ultrasonically measureable parameters including any one or more of: attenuation vs. depth (e.g. depth along a transmit/receive path axis of the ultrasound system, depth within the blood vessel, depth from an exterior surface of the body region upon which an ultrasound system is placed, etc.), imaging center frequency, hematocrit, vessel pressure, blood velocity, scatterer size and density, and/or Doppler power spectrum. Additionally or alternatively, parameters correlating with $\beta$ can be used in estimating $\beta$, the correlating parameters including one or more of flow velocity, volumetric flow rate, attenuation vs. depth, turbulence, local temperature, blood-oxygen content, administered drug dosage, age, gender, ethnicity, and/or other suitable correlating parameters. In a specific example, determining an estimated backscatter efficiency coefficient can be based on blood vessel flow velocity and ultrasound signal attenuation in relation to depth, using a correlation appropriate to the medium including the reflective plane. However, values of $\beta$ can be determined by, derived from, and/or based on any suitable data.

In another variation of Block S150, determining an absolute attribute value can include measuring values associated with transmitted ultrasound power on an opposing vessel wall side opposite the vessel wall side proximal the ultrasound system. In this variation, determining an absolute attribute value can exclude measuring values associated with same-side echoes. Measured values associated with transmitted ultrasound power on the opposing vessel wall side can be used in determining absolute values of attribute values (e.g., internal vessel pressure) with corresponding attenuation, scatter, and/or back-reflection coefficients. In a specific example, the target vessel includes a first side opposing a second side, where providing a push pulse includes providing the push pulse at a location proximal the first side, where determining the push pulse-dependent value includes measuring transmitted ultrasound power at a location proximal the second side, and the method 100 further including determining an absolute value of the pressure value based on the transmitted ultrasound power at the location proximal the second side, an attenuation coefficient, a scatter coefficient, and a back-reflection coefficient, wherein generating the pressure waveform comprises generating the pressure waveform based on the absolute value of the pressure value. However, determining absolute attribute values based on measuring values associated with transmitted ultrasound power can be performed in any suitable manner.

3.6 Generating an Analysis.

The method 100 can additionally or alternatively include Block S160, which recites: generating an analysis of at least one of an attribute value and an attribute value waveform. Block S160 functions to analyze one or more generated values for assessing physiological health of a user. Generating an analysis can include one or more of: generating a diagnostic analysis (e.g., providing a risk level and/or severity level associated with cardiovascular health), generating a therapeutic recommendation (e.g., to improve the cardiovascular health of a user), and/or generating a treatment response analysis (e.g., in evaluating the efficacy and potential modifications to be made for a implemented treatment). However, any suitable analysis can be generated for evaluating physiological health. Generating an analysis is preferably based on one or more of an attribute value (e.g., generated as in Block S130), an attribute value waveform (e.g., generated as in Block S140), and/or absolute attribute values (e.g., generated as in Block S150). Additionally or alternatively, an analysis can be generated from, determined by, and/or based on any other suitable data in relation to the method 100.

In relation to Block S160, portions of generating an analysis can be performed in real-time (e.g., as attribute values, attribute value waveforms, absolute attribute values, etc. are generated), in response to satisfaction of a data characteristic condition (e.g., a threshold amount of data collected, threshold types of data collected, etc.), manually triggered, automatically triggered, and/or performed at any suitable time. For example, generating an analysis can be performed on a set of generated attribute values (e.g., a set of generated blood pressures) and/or a set of generated attribute value waveforms (e.g., a set of generated blood pressure waveforms corresponding to different temporal indicators), simultaneously, such as through leveraging parallel computing principles, which can thereby improve the efficiency of the processing system. However, different portions of generating the analysis can be performed contemporaneously, simultaneously, in series, in parallel, and/or with any suitable temporal relationship relative each other. Different portions of generating an analysis S160 can be performed at a same processing system (e.g., a processing system used in performing Blocks S120, S130, S140, and/or S150, a processing subsystem of an ultrasound system, etc.), a different processing system, a remote server, and/or any suitable component.

In a variation of Block S160, generating an analysis can include generating an analysis using an attribute value analysis model. Attribute value analysis models can include diagnostic analysis models, therapy recommendation models, treatment response models and/or any other suitable models for generating medically relevant information based on attribute values, attribute value waveforms, and/or any other suitable information. Attribute value analysis models can incorporate probabilistic properties, heuristic properties, deterministic properties, and/or any other suitable properties for generating an analysis. In an example, generating an analysis can include leveraging a decision tree model incorporating attribute values and/or characteristics derived from attribute value waveforms. In another example, generating an analysis includes employing a machine learning model (e.g., using a machine learning approach described in Section 4) for predicting diagnoses, treatment recommendations, and/or other suitable physiological information based on features derived from push pulse-dependent values, attribute values, attribute value waveforms, and/or other suitable information. However, Generating an analysis using an attribute value analysis model can be performed in any suitable manner.

In another variation of Block S160, generating an analysis can include manually generating an analysis. Manually generating an analysis preferably includes manual review of generated attribute values, attribute value waveforms, and/or absolute attribute values by a care provider, a researcher, a guardian, and/or other suitable entity. In an example, manually generating an analysis can include processing generated values relating to the method 100 into a reviewable form, and transmitting the reviewable form of the processed generated values to a care provider for analysis.

However, generating an analysis S160 can be performed in any suitable manner.

3.7 Presenting Information.

The method 100 can additionally or alternatively include Block S170, which recites: presenting information derived from the analysis. Block S170 functions to present information from the analysis to inform an entity of physiological health status concerning a user. Presented information is preferably derived from an analysis (e.g., diagnostic results, therapy recommendation, treatment response analysis, etc.) generated as in Block S160, but can additionally or alternatively include raw data (e.g., raw attribute values, raw attribute value waveforms, raw push pulse-dependent values, raw correlation curves, etc.), supplemental information (e.g., user behavioral characteristics, user demographic characteristics, etc.), social comparison information (e.g., comparisons of physiological health in relation to other users, other subgroups, etc.), and/or any other suitable information. Presented information can possess any number or combination of forms, including numerical (e.g., numerical attribute values, risk values, condition severity values, etc.), verbal (e.g., verbal indications of cardiovascular risk and/or disease, verbal recommendations, etc.), graphical (e.g., colors indicating risk state, educational graphics, correlation curves, waveforms, etc.), and/or any suitable form.

Regarding Block S170, Information is preferably presented to a user at a user device, but can additionally or alternatively be presented to a care provider (e.g., at a care provider device), a researcher (e.g., a researcher implementing the method 100 in a research setting), and/or any other suitable entity through any suitable medium. An entity can be presented with information transmitted by a remote server, a communications module of an ultrasound system, and/or through any suitable component.

In relation to Block S170, presenting information derived from the analysis can include presenting the information based on rules (e.g., notification preferences set by a user, rules established by a care provider, by a guardian, etc.), time (e.g., notification at set frequencies, times of day, etc.), steps (e.g., presenting an analysis in response to generating the analysis as in Block S160), and/or any other suitable criteria.

As shown in FIG. 3A, in a first variation of Block S170, presenting an analysis can include automatically notifying an entity through an application executing on a corresponding mobile computing device. Automatic notifications can be transmitted from a remote server to a mobile computing device associated with a user, a guardian, a care provider, and/or any other suitable entity. Automatic notifications can take the form of a native application notification, a text message, a web interface, an application interface, and/or any other suitable form. However, automatically notifying an entity can be performed in any suitable manner In a second variation of Block S170, presenting an analysis can include automatically presenting an alert in response to a characteristic of the analysis of the cardiovascular parameter exceeding a threshold (e.g., a blood pressure measurement exceeding a threshold). Thresholds can be established (e.g., by a care provider, by a guardian, by a user, by a third party, etc.) for characteristics of any suitable model, dataset, and/or information in relation to the method 100 However, presenting an alert based on thresholds can be performed in any suitable manner.

Additionally or alternatively, presenting information derived from the analysis can be performed in any suitable fashion.

The method 100 can, however, include any other suitable blocks or steps configured to facilitate provision of an ultrasound system and/or push pulses, measuring push pulse-dependent values, generating attribute values (e.g., relative attribute values, absolute attribute values), attribute value waveforms, associated analyses (e.g., generating diagnostic analyses, generating therapy recommendations, generating treatment response analyses), presenting corresponding information, and/or other relevant operations.

4. System.

Figure 11:
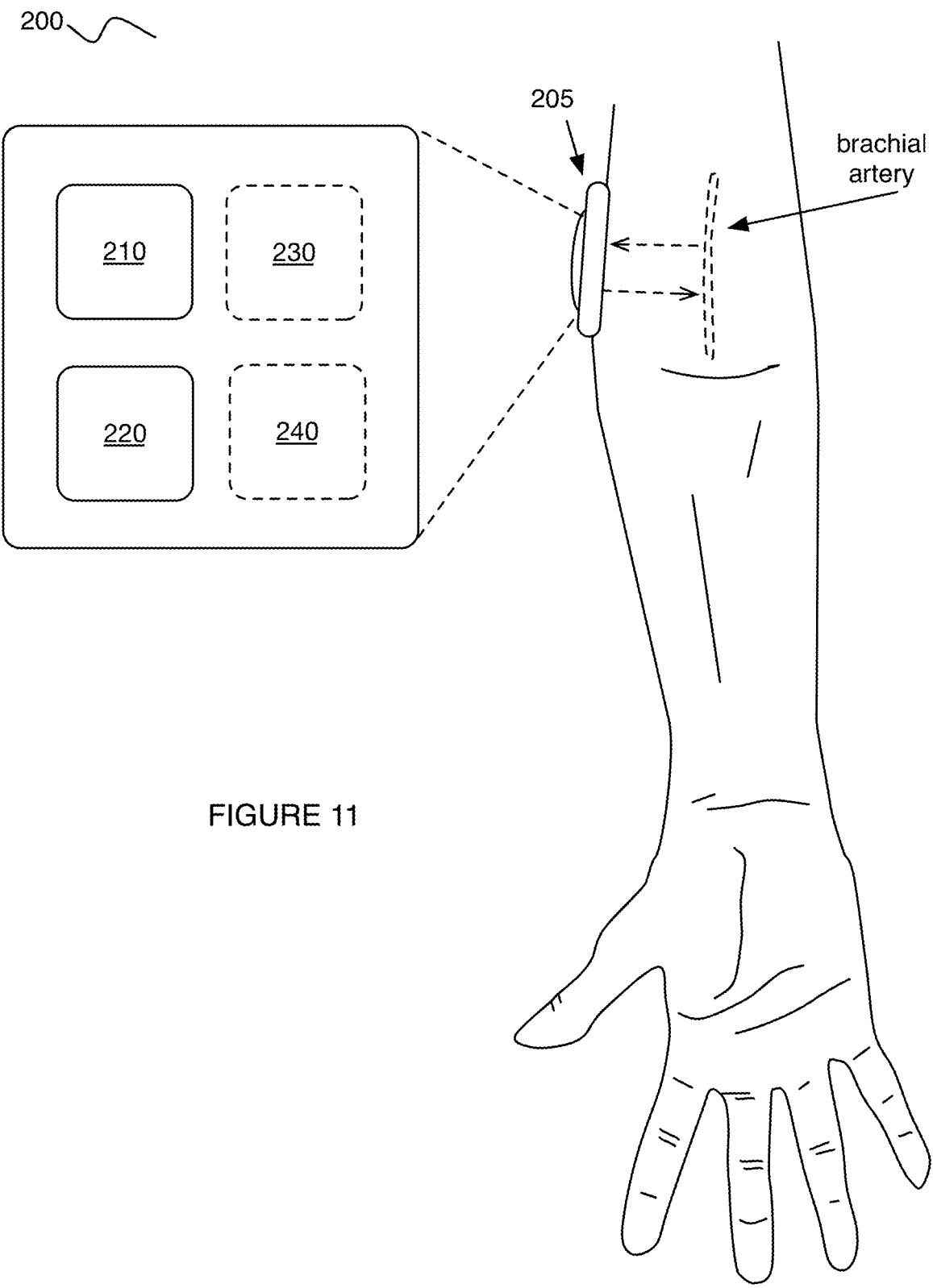
FIGS. 11, 12A-12C, and 13A-13D depict variations of an embodiment of a system for using ultrasound in determining attribute values associated with a vessel of a user.
Figure 12A:
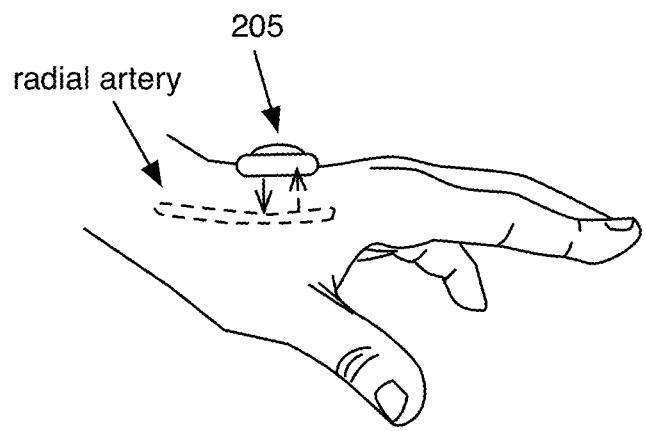
Figure 12B:
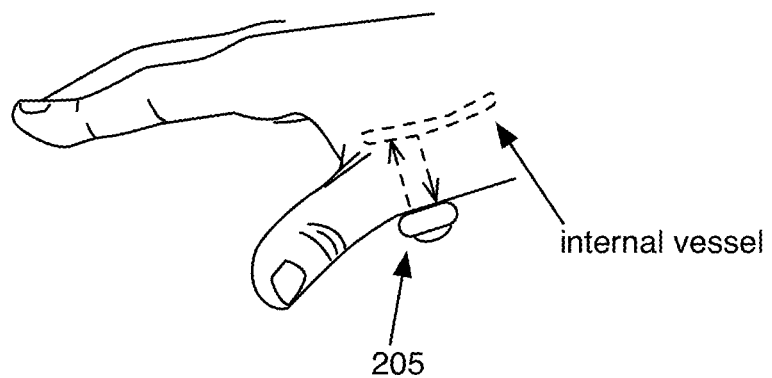
Figure 12C:
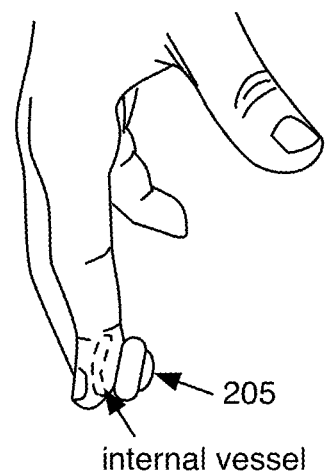

As shown in FIG. 11, an embodiment of a system 200 for evaluating vessel attribute values of a vessel of a user can include an ultrasound system 205, which can include an ultrasound transducer 210, a processing subsystem 220, a communications module 230, and/or a user interface 240. In variations, the system 200 functions to leverage an ultrasound technology-based system to evaluate physiological health (e.g., cardiovascular-related health states) of users by analyzing vessel attribute values (e.g., internal pressure of a blood vessel). The system 200 can additionally or alternatively function to diagnose, monitor, recommend therapies, alert users and/or integrate with electronic health record (EHR) systems in relation to evaluated physiological parameters (e.g., blood pressure, blood pressure variation over time, etc.).

In some embodiments, the system 200 and/or components of the system 200 can additionally or alternatively include or communicate data to and/or from: a user database (storing user account information, user profiles, user health records, user demographic information, associated care provider information, associated guardian information, user device information, previously presented information to the user, etc.), an analysis database (storing computational models, collected data, historical data, public data, simulated data, generated data, generated analyses, diagnostic results, therapy recommendations, etc.), and/or any other suitable computing system.

Database(s) and/or portions of the method 100 can be entirely or partially executed, run, hosted, or otherwise performed by: a remote computing system (e.g., a server, at least one networked computing system, stateless computing system, stateful computing system, etc.), an ultrasound system (e.g., a processing subsystem of an ultrasound system), a user device, a care provider device (e.g., a device of a care provider associated with a user), a machine configured to receive a computer-readable medium storing computer-readable instructions, or by any other suitable computing system possessing any suitable component (e.g., a graphics processing unit, a communications module, etc.). However, the components of the system 200 can be distributed across machine and cloud-based computing systems in any other suitable manner.

Devices implementing at least a portion of the method 100 can include one or more of: an ultrasound system, smartwatch, smartphone, a wearable computing device (e.g., head-mounted wearable computing device), tablet, desktop, a supplemental sensor, a biosignal detector, a medical device, and/or any other suitable device. All or portions of the method 100 can be performed by one or more of: a native application, web application, firmware on the device, plug-in, and any other suitable software executing on a device. Device components used with the method 100 can include an input (e.g., keyboard, touchscreen, etc.), an output (e.g., a display), a processor, a transceiver, and/or any other suitable component, wherein data from the input device(s) and/or output device(s) can be generated, analyzed, and/or transmitted to entities for consumption (e.g., for a user to assess their diagnostic results, microbiome insights, and/or therapy recommendations.) Communication between devices and/or databases can include wireless communication (e.g., WiFi, Bluetooth, radiofrequency, etc.) and/or wired communication.

Components of the system 200 (e.g., a processing subsystem of an ultrasound system) and/or any other suitable component of the system 200, and/or any suitable portion of the method 100 can employ machine learning approaches including any one or more of: supervised learning (e.g., using logistic regression, using back propagation neural networks, using random forests, decision trees, etc.), unsupervised learning (e.g., using an Apriori algorithm, using K-means clustering), semi-supervised learning, reinforcement learning (e.g., using a Q-learning algorithm, using temporal difference learning), and any other suitable learning style. Each module of the plurality can implement any one or more of: a regression algorithm (e.g., ordinary least squares, logistic regression, stepwise regression, multivariate adaptive regression splines, locally estimated scatterplot smoothing, etc.), an instance-based method (e.g., k-nearest neighbor, learning vector quantization, self-organizing map, etc.), a regularization method (e.g., ridge regression, least absolute shrinkage and selection operator, elastic net, etc.), a decision tree learning method (e.g., classification and regression tree, iterative dichotomiser 3, C4.5, chi-squared automatic interaction detection, decision stump, random forest, multivariate adaptive regression splines, gradient boosting machines, etc.), a Bayesian method (e.g., naïve Bayes, averaged one-dependence estimators, Bayesian belief network, etc.), a kernel method (e.g., a support vector machine, a radial basis function, a linear discriminate analysis, etc.), a clustering method (e.g., k-means clustering, expectation maximization, etc.), an associated rule learning algorithm (e.g., an Apriori algorithm, an Eclat algorithm, etc.), an artificial neural network model (e.g., a Perceptron method, a back-propagation method, a Hopfield network method, a self-organizing map method, a learning vector quantization method, etc.), a deep learning algorithm (e.g., a restricted Boltzmann machine, a deep belief network method, a convolution network method, a stacked autoencoder method, etc.), a dimensionality reduction method (e.g., principal component analysis, partial lest squares regression, Sammon mapping, multidimensional scaling, projection pursuit, etc.), an ensemble method (e.g., boosting, boostrapped aggregation, AdaBoost, stacked generalization, gradient boosting machine method, random forest method, etc.), and any suitable form of machine learning algorithm. Each processing portion of the method 100 can additionally or alternatively leverage: a probabilistic module, heuristic module, deterministic module, or any other suitable module leveraging any other suitable computation method, machine learning method or combination thereof.

4.1 Ultrasound System.

The system 200 includes an ultrasound system 205, which can additionally or alternatively include an ultrasound transducer 210, a processing subsystem 220, a communications module 230, a user interface 240, and/or any other suitable components. The ultrasound system 205 functions to perform one or more portions of the method 100, including one or more of providing push pulses characterized by a set of push pulse parameters, measuring a push pulse-dependent value, and/or generating corresponding attribute values and/or attribute value waveforms. The ultrasound system 205 and/or components of the ultrasound system 205 can be in the form of a patch, a touch-pad, a probe, and/or possess any suitable form. The ultrasound system 205 is preferably a non-cuff based system, but can additionally or alternatively incorporate utilization of a blood pressure measurement cuff. However, components of the ultrasound system 205 can have any suitable form, shape, and/or configuration. The ultrasound system 205 preferably uses DC power input, and can run from a universal supply and/or a battery pack, which can vary depending on context and application. However, components of the ultrasound system can be powered in any suitable manner.

Figure 13A:
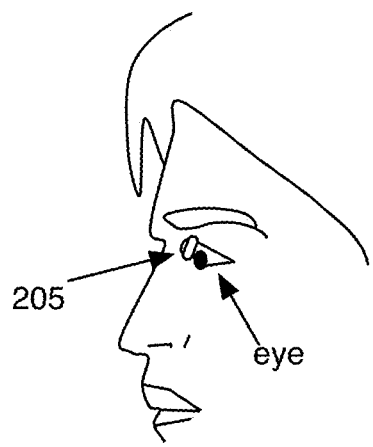
Figure 13B:
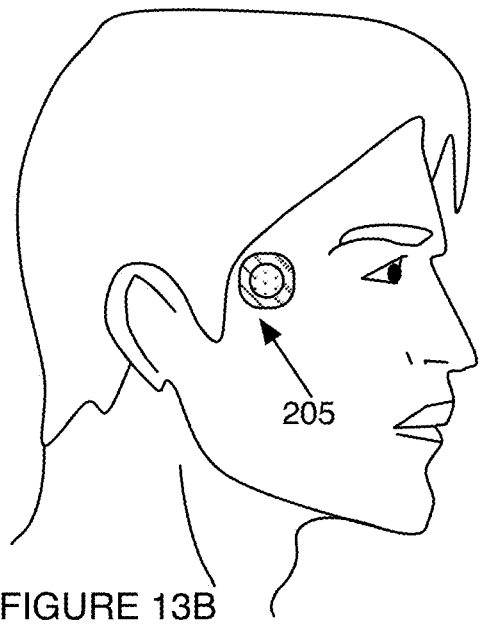
Figure 13C:
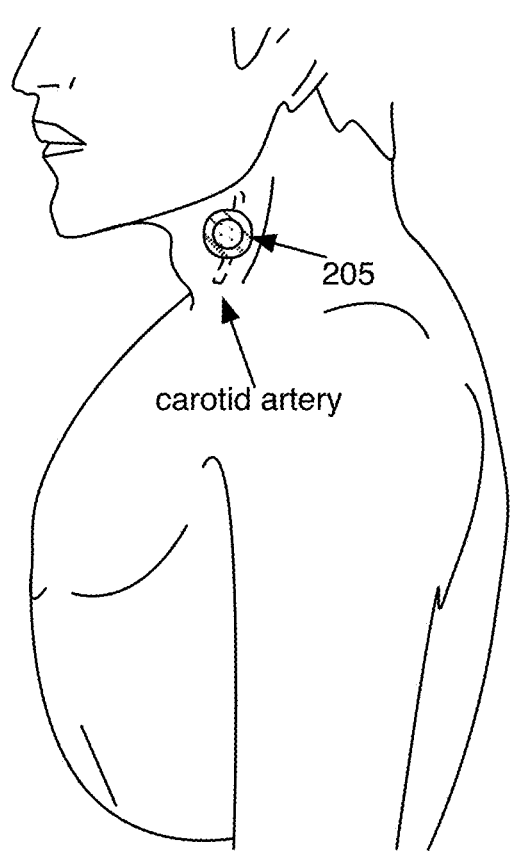
Figure 13D:
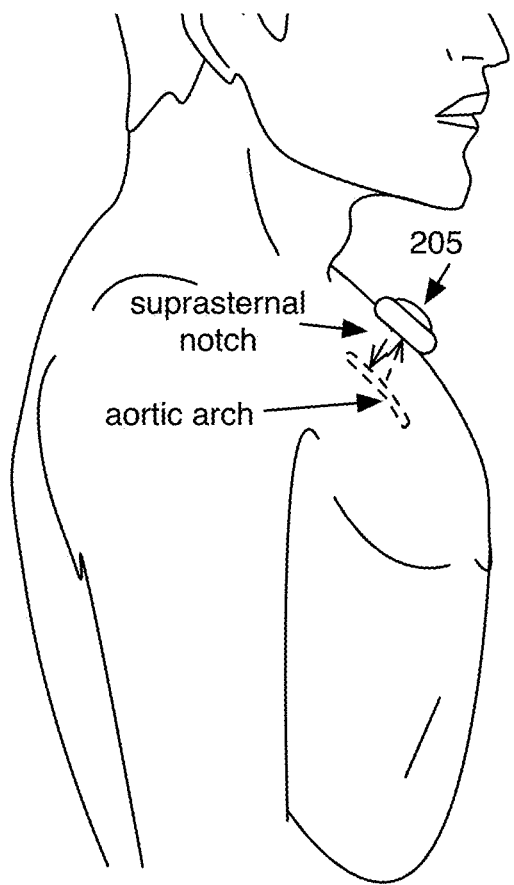

As shown in FIGS. 12A-13D, components of the ultrasound system 205 can be placed, positioned, arranged, and/or coupled at any suitable body region of a user, including: the user's arm (e.g., near internal vessels of the hand, near a radial artery, near a brachial artery, etc.) as in FIGS. 12A-12D, head (e.g., outside an eyelid, near a temple, etc.) as in FIGS. 13A-13B, torso (e.g., at a suprasternal notch, near an aortic arch, etc.) as in FIG. 13D, neck (e.g., near a carotid artery, etc.) as in FIG. 13C, and/or any other internal and/or external body region of the user.

Components of the ultrasound system can be proximal each other (e.g., housed under a single housing), distant each other (e.g., an ultrasound transducer coupled to the body region and an processing subsystem positioned distant the body region), and/or have any suitable positional relationship with each other.

In a variation of the ultrasound system 205, the ultrasound system 205 can be implanted through a cart-based ultrasound platform. For example, during a transesophageal echocardiogram survey, pressure in the chambers of the heart could be measured. As another example, uterine pressure could be measured during pregnancy. Additionally or alternatively, implementation of the ultrasound system 205 through a cart-based ultrasound platform can be configured in any suitable fashion.

However, the ultrasound system 205 and/or components of the ultrasound system 205 (e.g., ultrasound transducer 210, processing subsystem 220, communications module 230, user interface 240, etc.), can additionally or alternatively include any elements analogous to those described in U.S. application Ser. No. 13/655,191 entitled "System and Method for Unattended Monitoring of Blood Flow," filed 18 Oct. 2012, and U.S. application Ser. No. 13/854,824, entitled "Ultrasound System and Method of Manufacture", filed 1 Apr. 2013, which are herein each incorporated in their entirety by this reference, but the ultrasound system 205 and/or components of the ultrasound system 205 can have any suitable configuration.

4.1.A Ultrasound Transducer.

As shown in FIG. 11, the ultrasound system 205 can additionally or alternatively include an ultrasound transducer 210, which functions to transmit, receive, and/or convert (e.g., into electrical signals) ultrasound waves for push pulse provision and corresponding measurement. The ultrasound system 205 can include one or more ultrasound transducers 210. An ultrasound transducer 210 is preferably in the form of a Capacitive Micromachined Ultrasonic Transducers (CMUT), but can additionally or alternatively include any other suitable form (e.g., piezoelectric transducers, etc.). CMUTs can preferably leverage high volume processes and low cost structure analogous to integrated circuits, while allowing the integration of electronics directly in the transducer array. In specific examples, leveraging CMUTs can thus minimize cabling and simplify the readout unit, facilitating a compact, lightweight component. However, ultrasound transducers can possess any suitable property Ultrasound transducers 210 preferably include an array of transmitter elements, which can function to facilitate multiplexing and/or lead-count-reduction schemes. With respect to arrays of transmitter elements, ultrasound transducers 210 can preferably include analog switches to statically select different groups of elements during sequential transmit cycles, include analog adders & digitally-controlled switch banks to scan variable-width apertures across the array, and/or include time-division multiplexing circuits to continuously sample multiple elements onto one receive channel. However, ultrasound transducers 210 can be configured in any suitable fashion.

4.1.B Processing Subsystem.

As shown in FIG. 11, the ultrasound system 205 can additionally or alternatively include a processing subsystem 220, which can function to process collected signals (e.g., push pulse-dependent values), generate attribute values (e.g., relative attribute values, absolute attribute values, etc.), generate attribute value waveforms, generate an analysis, facilitate presentation of information derived from the analysis, and/or perform other processing operations relating to the method 100. A processing subsystem 220 is preferably electrically connected with the ultrasound transducer 205, but can be connected in any suitable fashion to any suitable component of the ultrasound system 205 and/or system 200.

The processing subsystem 220 is preferably in the form of a single printed circuit board (PCB), which can preferably satisfy, insonification, digitization, and digital signal-processing requirements associated with the method 100. Leveraging a single PCB for the processing subsystem 220 preferably facilitates construction of a low-cost, compact, and durable processing subsystem 220. PCB architecture is preferably compartmentalized into six functional blocks, including transmit pulsers, analog frontend (AFE), analog-to-digital conversion (ADC), DSP, digital I/O (including indicators, Bluetooth transceiver, and service port), and power distribution. Additionally or alternatively, the processing subsystem 220 and/or PCB construction can include an amplifier, electrical connectors, and/or any other suitable components. However, the processing subsystem 220 can be configured in any suitable fashion.

4.1.C Communications Module.

As shown in FIG. 11, the ultrasound system 205 can additionally or alternatively include a communications module 230, which functions to transmit and/or receive data in relation to evaluating physiological health of a user using ultrasound. The communications module 230 is preferably electrically connected with a processing subsystem 220 of the ultrasound system 205, such that datasets generated by the processing subsystem 220 can be transmitted to a suitable destination. Suitable destinations include a remote server, an additional processing system, and/or any other suitable destination. In an example, push pulse-dependent values are measured and processed by the ultrasound system 205, where the communications module 230 of the ultrasounds system is configured to transmit the push pulse-dependent value dataset to a remote server configured to determine attribute values and/or an attribute value waveform in generating an analysis of physiological health. Communication through the communications module can be wired, wireless (e.g., through Bluetooth, WiFi, etc.), and/or through any suitable means. However, a communications module 230 can be configured in any suitable manner.

4.1.D User Interface.

As shown in FIG. 11, the ultrasound system 205 can additionally or alternatively include a user interface 240, which can function to present generated data (e.g., generated attribute values, generated attribute value waveforms, etc.), information derived from generated analyses (e.g., diagnostic results, therapy recommendations, treatment response analyses, etc.), and/or other suitable information to a user. The user interface 240 can additionally or alternatively function to present instructions (e.g., instructions for placing the ultrasound system at a body region of the user, instructions for recoupling the ultrasound system) and/or notifications (e.g., alerts of an uncoupled state of the ultrasound system with the body region of the user, warnings regarding cardiovascular parameters exceeding safety ranges, etc.). User preferences (e.g., notification preferences, desired physiological health parameters, etc.), push pulse parameters, and/or other suitable conditions can be selected at the user interface. However, the user interface 240 can provide a venue through which a user can personalize the ultrasound system 205 in any suitable fashion.

The user interface 240 can be a graphical user interface (GUI), a voice user interface (e.g., a virtual assistant providing oral communication), a touch-based interface (e.g., a capacitive touch interface), and/or any other suitable type of user interface 240.

A communication channel preferably exists between the user interface 240 and a processing subsystem 220, such that information generated by the processing subsystem can be presented at the user interface. Additionally or alternatively, a communication link can be established between the user interface 240 and a communications module 230, such that information transmitted and/or received by the communications module 230 can be presented at the user interface 240.

However, the user interface 240 can be configured in any suitable fashion.

The method 100 and/or system 200 of the embodiments can be embodied and/or implemented at least in part as a machine configured to receive a computerreadable medium storing computer-readable instructions. The instructions can be executed by computer-executable components integrated with the application, applet, host, server, network, website, communication service, communication interface, hardware/firmware/software elements of a patient computer or mobile device, or any suitable combination thereof. Other systems and methods of the embodiments can be embodied and/or implemented at least in part as a machine configured to receive a computer-readable medium storing computer-readable instructions. The instructions can be executed by computer-executable components integrated with apparatuses and networks of the type described above. The computer-readable medium can be stored on any suitable computer readable media such as random access memory (RAMs), read-only memory (ROMs), flash memory, electrically erasable programmable read-only memory (EEPROMs), optical devices (e.g., compact disc (CD), digital versatile disc (DVD), etc.), hard drives, floppy drives, or any suitable device. The computer-executable component can be a processor, though any suitable dedicated hardware device can (alternatively or additionally) execute the instructions.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

As a person skilled in the art will recognize from the previous detailed description and from the figures and claims, modifications and changes can be made to the embodiments of the invention without departing from the scope of this invention as defined in the following claims.

We claim:

1. A method for using ultrasound for evaluating blood pressure of a user, the method comprising:
providing an ultrasound system configured to be placed at a body region proximal a blood vessel of the user;
generating a correlation between a set of push pulse pressure parameters and a set of displacement values associated with the blood vessel, the correlation corresponding to a sampling time period, wherein generating the correlation comprises, for each of the set of push pulse pressure parameters:
from the ultrasound system, emitting acoustic energy with a push pulse towards the blood vessel, the push pulse characterized by one of the set of push pulse pressure parameters and manifesting proximal the blood vessel,
determining a displacement value based on displacement of the blood vessel by the push pulse, the set of displacement values comprising the displacement value;

wherein the set of push pulse pressure parameters comprises:
  a first subset of the set of push pulse pressure parameters, each push pulse pressure parameter of the first subset below a pressure in the blood vessel at the sampling time period, and
  a second subset of the set of push pulse pressure parameters, each push pulse pressure parameter of the second subset above the pressure in the blood vessel at the sampling time period,
generating a blood pressure value from the blood vessel based on the correlation between the set of push pulse pressure parameters and the set of displacement values
generating a blood pressure waveform from the blood pressure value and a set of supplemental blood pressure values corresponding to a set of time periods distinct from the sampling time period;
generating a set of supplementary correlations corresponding to the set of time periods, wherein generating the set of supplementary correlations comprises for each time period of the set of time periods:
  generating a supplementary correlation between a set of supplementary push pulse pressure parameters and a set of supplemental displacement values associated with the blood vessel, wherein the set of supplementary correlations comprises the supplementary correlation, and wherein generating the correlation comprises for each supplementary push pulse pressure parameter of the set of supplementary push pulse pressure parameters:
    providing a supplementary push pulse with the ultrasound system, the supplementary push pulse characterized by the supplementary push pulse pressure parameter, and
    determining a supplemental displacement value based on the push pulse, the set of supplemental displacement values comprising the supplementary displacement value; and
  generating a supplemental blood pressure value based on the supplementary correlation between the set of supplementary push pulse pressure parameters and the set of supplemental displacement values, wherein the set of supplemental blood pressure values comprises the supplemental blood pressure value.

2. The method of claim 1, wherein the transition region corresponds to a time window of the time period and comprises a transition push pulse pressure parameter of the set of push pulse pressure parameters, wherein the transition push pulse parameter directly corresponds to a pressure in the blood vessel associated with the time window.

3. The method of claim 2, wherein the transition push pulse pressure parameter is substantially equal to the pressure in the blood vessel at the time window.

4. The method of claim 2, wherein the transition push pulse pressure parameter differs from the pressure in the blood vessel by approximately a known pressure delta at the time window, the known pressure delta associated with a medium proximal the blood vessel.

5. The method of claim 1, wherein emitting acoustic energy comprises emitting acoustic energy characterized by a known push pulse power parameter, the method further comprising determining an absolute value of the blood pressure value based on the known push pulse power parameter and an attenuation coefficient.

6. The method of claim 5, further comprising determining an estimated backscatter efficiency coefficient based on blood vessel flow velocity and ultrasound signal attenuation in relation to depth, wherein the estimated backscatter efficiency coefficient is used in determining the absolute value of the blood pressure value.

7. The method of claim 1, further comprising:
generating a set of vessel diameter measurements of the blood vessel, comprising:
  measuring a vessel diameter corresponding to the sampling time period, the set of vessel diameter measurements comprising the vessel diameter, and
  measuring a set of supplemental vessel diameters, each corresponding to a distinct time period of the set of time periods, the set of vessel diameter measurements comprising the set of supplemental vessel diameters; and
generating a correlation between the set of vessel diameter measurements and a set of blood pressure values comprising the blood pressure value and a set of supplemental blood pressure values.

8. The method of claim 7, further comprising:
measuring a subsequent vessel diameter at a later time period subsequent the sampling time period and the set of time periods; and
determining a first estimated blood pressure value corresponding to the later time period, based on the subsequent vessel diameter and the correlation between the set of vessel diameter measurements and the set of blood pressure values.

9. The method of claim 8, further comprising:
generating an updated correlation between an updated set of vessel diameter measurements and an updated set of blood pressure values, the updated correlation associated with a set of updated time periods subsequent the sampling time period and the set of time periods; and
determining a second estimated blood pressure value based on the subsequent vessel diameter and the updated correlation, wherein the second estimated blood pressure value is distinct from the first estimated blood pressure value.

10. The method of claim 1, wherein emitting the acoustic energy with the push pulse comprises providing each push pulse characterized by the first subset of push pulse pressure parameters prior to providing each push pulse characterized by the second subset of push pulse pressure parameters.

11. The method of claim 10, wherein each push pulse parameter of the set of push pulse parameters is stepwise incremented relative a preceding push pulse parameter, wherein the stepwise increment is characterized by an increment value based on a final measurement resolution value.

12. The method of claim 1, wherein the set of push pulse parameters comprises a magnitude of the acoustic energy.

13. A method for using ultrasound for evaluating pressure of a vessel of a user, the method comprising:
providing an ultrasound system configured to be placed at a body region proximal the vessel of the user;
generating a correlation between a set of push pulse parameters and a set of push pulse-dependent values associated with the vessel, the correlation corresponding to a sampling time period, wherein generating the correlation comprises for each of the set of push pulse parameters:
  from the ultrasound system, providing a push pulse characterized by one of the set of push pulse parameters, the push pulse positioned proximal the blood vessel, and determining a push pulse-dependent value based on the push pulse, the set of push pulse-dependent values comprising the push pulse-dependent value;

wherein the set of push pulse pressure parameters comprises:
- a first subset of the set of push pulse pressure parameters, each push pulse pressure parameter of the first subset below a pressure in the blood vessel at the sampling time period, and
- a second subset of the set of push pulse pressure parameters, each push pulse pressure parameter of the second subset above the pressure in the blood vessel at the sampling time period, generating a pressure value from the vessel based on the correlation between the set of push pulse parameters and the set of push pulse-dependent values; and generating a pressure waveform from the pressure value and a set of supplemental pressure values corresponding to a set of time periods distinct from the sampling time period;

generating a set of supplementary correlations corresponding to the set of time periods, wherein generating the set of supplementary correlations comprises for each time period of the set of time periods:
- generating a supplementary correlation between a set of supplementary push pulse parameters and a set of supplemental push pulse-dependent values associated with the vessel, wherein the set of supplementary correlations comprises the supplementary correlation, and wherein generating the supplementary correlation comprises for each supplementary push pulse parameter of the set of supplementary push pulse parameters:
  - providing a supplementary push pulse with the ultrasound system, the supplementary push pulse characterized by the supplementary push pulse parameter, and
  - determining a supplemental push pulse-dependent value based on the push pulse, the set of supplemental push pulse-dependent values comprising the supplementary push pulse-dependent value; and
- generating a supplemental pressure value based on the supplementary correlation between the set of supplementary push pulse parameters and the set of supplemental push pulse-dependent values, wherein the set of supplemental pressure values comprises the supplemental pressure value.

14. The method of claim 13, wherein the set of push pulse-dependent values comprise at least one of depth of vessel deflection, diameter of deflected vessel region, and shear wave velocity, wherein generating the correlation comprises associating a push pulse parameter of the set of push pulse parameters with the at least one of the depth of vessel deflection, the diameter of deflected vessel region, and the shear wave velocity.

15. The method of claim 13, wherein generating the pressure value comprises identifying a transition push pulse parameter of the set of push pulse parameters, wherein the transition push pulse parameter corresponds to a time window of the sampling time period, and wherein a pressure of the push pulse is substantially equal to a pressure in the vessel at the time window.

16. The method of claim 13, wherein the vessel comprises a first side opposing a second side, wherein providing the push pulse comprises providing the push pulse at a location proximal the first side, wherein determining the push pulse-dependent value comprises measuring transmitted ultrasound power at a location proximal the second side, and the method further comprising determining an absolute value of the pressure value based on the transmitted ultrasound power at the location proximal the second side, an attenuation coefficient, a scatter coefficient, and a back-reflection coefficient, wherein generating the pressure waveform comprises generating the pressure waveform based on the absolute value of the pressure value.

17. The method of claim 13, further comprising:
- generating a vessel pressure correlation between (1) the pressure value and the set of supplemental pressure values, and (2) corresponding push pulse-dependent values;
- determining a subsequent push pulse-dependent value at a later time period subsequent the sampling time period and the set of time periods; and
- determining an estimated pressure value of the vessel corresponding to the later time period, based on the subsequent push pulse-dependent value and the vessel pressure correlation.

18. The method of claim 13, wherein the ultrasound system comprises an ultrasound transducer patch coupled to the body region, and an electronics subsystem configured to adjust a transmission direction for an array of transmitter elements of the transducer patch, wherein providing the push pulse comprises:
- adjusting the transmission direction towards the vessel, and
- providing the push pulse based on the transmission direction.

19. The method of claim 13, wherein the sampling time period is shorter than a reference time period corresponding to a duration for a pressure of the vessel to change by a predetermined target accuracy percent.

20. The method of claim 13, wherein the vessel comprises at least one of a blood vessel, a heart chamber, and a bladder of the user, wherein the pressure waveform corresponds to pressure within the at least one of the blood vessel, the heart chamber, and the bladder of the user.

21. A method for using ultrasound for evaluating pressure of a vessel of a user, the method comprising:
- providing an ultrasound system configured to be placed at a body region proximal the vessel of the user, wherein the vessel comprises a first side opposing a second side;
- generating a correlation between a set of push pulse parameters and a set of push pulse-dependent values associated with the vessel, the correlation corresponding to a sampling time period, wherein generating the correlation comprises for each of the set of push pulse parameters:
  - from the ultrasound system, providing a push pulse characterized by one of the set of push pulse parameters, the push pulse positioned proximal the blood vessel, wherein providing the push pulse comprises providing the push pulse at a location proximal the first side, and
  - determining a push pulse-dependent value based on the push pulse, the set of push pulse-dependent values comprising the push pulse-dependent value, wherein determining the push pulse-dependent value comprises measuring transmitted ultrasound power at a location proximal the second side;

wherein the set of push pulse pressure parameters comprises:
- a first subset of the set of push pulse pressure parameters, each push pulse pressure parameter of the first subset below a pressure in the blood vessel at the sampling time period, and a second subset of the set of push pulse pressure parameters, each push pulse pressure parameter of the second subset above the pressure in the blood vessel at the sampling time period, generating a pressure value from the vessel based on the correlation between the set of push pulse parameters and the set of push pulse-dependent values;

determining an absolute value of the pressure value based on the transmitted ultrasound power at the location proximal the second side, an attenuation coefficient, a scatter coefficient, and a back-reflection coefficient; and generating a pressure waveform from the pressure value and a set of supplemental pressure values corresponding to a set of time periods distinct from the sampling time period, wherein generating the pressure waveform comprises generating the pressure waveform based on the absolute value of the pressure value.

* * * * *